(12) United States Patent
Chen et al.

(10) Patent No.: US 10,858,372 B2
(45) Date of Patent: Dec. 8, 2020

(54) AMORPHOUS SOLID FORM OF A BET PROTEIN INHIBITOR

(71) Applicant: Incyte Corporation, Wilmington, DE (US)

(72) Inventors: Shili Chen, Newark, DE (US); William Frietze, Kennett Square, PA (US); Zhongjiang Jia, Kennett Square, PA (US); Pingli Liu, Wilmington, DE (US); Jiacheng Zhou, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/425,193

(22) Filed: May 29, 2019

(65) Prior Publication Data
US 2019/0300545 A1    Oct. 3, 2019

Related U.S. Application Data

(60) Continuation of application No. 15/913,248, filed on Mar. 6, 2018, now Pat. No. 10,329,305, which is a division of application No. 15/337,202, filed on Oct. 28, 2016, now abandoned, application No. 16/425,193, which is a division of application No. 15/337,202, filed on Oct. 28, 2016.

(60) Provisional application No. 62/248,040, filed on Oct. 29, 2015.

(51) Int. Cl.
*C07D 498/04* (2006.01)
*C07D 413/04* (2006.01)
*A61K 31/535* (2006.01)

(52) U.S. Cl.
CPC ........ *C07D 498/04* (2013.01); *C07D 413/04* (2013.01); *A61K 31/535* (2013.01)

(58) Field of Classification Search
CPC ............................ C07D 498/04; C07D 413/04
USPC ...................................................... 514/230.2
See application file for complete search history.

(56) References Cited

U.S. PATENT DOCUMENTS

| | | |
|---|---|---|
| 5,589,476 A | 12/1996 | Jegham et al. |
| 8,633,186 B2 | 1/2014 | Tachdjian et al. |
| 8,669,249 B2 | 3/2014 | Brown et al. |
| 9,012,642 B2 | 4/2015 | Haydar et al. |
| 9,227,985 B2 | 1/2016 | Combs et al. |
| 9,290,514 B2 | 3/2016 | Combs et al. |
| 9,309,246 B2 | 4/2016 | Rodgers et al. |

(Continued)

FOREIGN PATENT DOCUMENTS

| | | |
|---|---|---|
| CA | 2171579 | 9/1996 |
| CA | 2903881 | 9/2014 |

(Continued)

OTHER PUBLICATIONS

Ai et al., "Signal-induced Brd4 release from chromatin is essential for its role transition from chromatin targeting to transcriptional regulation," Nucleic Acids Res., 2011, 1-13.

(Continued)

*Primary Examiner* — Kevin E Weddington
(74) *Attorney, Agent, or Firm* — Fish & Richardson P.C.

(57) ABSTRACT

The present invention relates to an amorphous solid form of (4S)-7-(3,5-dimethylisoxazol-4-yl)-4-pyridin-2-yl-4,5-dihydroimidazo[1,5,4-de][1,4]benzoxazin-2(1H)-one, and processes for its preparation, which is an inhibitor of BET proteins such as BRD2, BRD3, BRD4, and BRD-t and is useful in the treatment of various diseases such as cancer.

14 Claims, 3 Drawing Sheets

(56) References Cited

U.S. PATENT DOCUMENTS

| | | |
|---|---|---|
| 9,315,501 B2 | 4/2016 | Yue et al. |
| 9,399,640 B2 | 7/2016 | Yue et al. |
| 9,527,864 B2 | 12/2016 | Combs et al. |
| 9,533,997 B2 | 1/2017 | Combs et al. |
| 9,540,368 B2 | 1/2017 | Combs et al. |
| 9,624,241 B2 | 4/2017 | Combs et al. |
| 9,737,516 B2 | 8/2017 | Yue et al. |
| 9,777,003 B2 | 10/2017 | Shepard et al. |
| 9,834,565 B2 | 12/2017 | Combs et al. |
| 9,850,257 B2 | 12/2017 | Combs et al. |
| 9,918,990 B2 | 3/2018 | Yue et al. |
| 9,938,294 B2 | 4/2018 | Combs et al. |
| 9,957,268 B2 | 5/2018 | Combs et al. |
| 9,957,628 B2 | 5/2018 | Combs et al. |
| 10,189,832 B2 | 1/2019 | Chen et al. |
| 10,227,359 B2 | 3/2019 | Combs et al. |
| 10,329,305 B2 | 6/2019 | Chen et al. |
| 10,442,803 B2 | 10/2019 | Rodgers et al. |
| 10,464,947 B2 | 11/2019 | Combs et al. |
| 10,472,358 B2 | 11/2019 | Combs et al. |
| 2002/0004510 A1 | 1/2002 | McCall et al. |
| 2007/0191447 A1 | 8/2007 | Kodo et al. |
| 2007/0244096 A1 | 10/2007 | Fox et al. |
| 2008/0306093 A1 | 12/2008 | Servant et al. |
| 2009/0306122 A1 | 12/2009 | Staehle et al. |
| 2013/0045229 A1 | 2/2013 | Iadonato et al. |
| 2013/0261109 A1 | 10/2013 | Miyoshi et al. |
| 2013/0281396 A1 | 10/2013 | McLure et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2014/0135316 A1 | 5/2014 | Albrecht et al. |
| 2014/0275030 A1 | 9/2014 | Combs et al. |
| 2015/0011540 A1 | 1/2015 | Combs et al. |
| 2015/0148342 A1 | 5/2015 | Yue et al. |
| 2015/0148372 A1 | 5/2015 | Yue et al. |
| 2015/0148375 A1 | 5/2015 | Yue et al. |
| 2015/0175604 A1 | 6/2015 | Rodgers et al. |
| 2015/0307493 A1 | 10/2015 | Combs et al. |
| 2016/0046650 A1 | 2/2016 | Combs et al. |
| 2016/0075721 A1 | 3/2016 | Combs et al. |
| 2016/0159817 A1 | 6/2016 | Combs et al. |
| 2016/0168148 A1 | 6/2016 | Shepard |
| 2016/0213654 A1 | 7/2016 | Yue et al. |
| 2016/0331749 A1 | 11/2016 | Bogdan et al. |
| 2017/0014418 A1 | 1/2017 | Yue et al. |
| 2017/0121347 A1 | 5/2017 | Chen et al. |
| 2017/0158689 A1 | 6/2017 | Combs et al. |
| 2017/0158710 A1 | 6/2017 | Combs et al. |
| 2017/0210754 A1 | 7/2017 | Combs et al. |
| 2017/0127985 A1 | 8/2017 | Combs et al. |
| 2017/0362229 A1 | 12/2017 | Chen et al. |
| 2018/0222920 A1 | 8/2018 | Combs et al. |
| 2018/0273546 A1 | 9/2018 | Chen et al. |
| 2018/0312506 A1 | 11/2018 | Combs et al. |
| 2018/0346481 A1 | 12/2018 | Combs et al. |
| 2019/0169186 A1 | 6/2019 | Chen et al. |
| 2019/0233435 A1 | 8/2019 | Combs et al. |

FOREIGN PATENT DOCUMENTS

| | | |
|---|---|---|
| CA | 2927567 | 4/2015 |
| CA | 2934788 | 7/2015 |
| CA | 2940554 | 9/2015 |
| CA | 2974153 | 8/2016 |
| CA | 3007168 | 6/2017 |
| CN | 105039258 | 11/2015 |
| CN | 105254635 | 1/2016 |
| EP | 0646583 | 4/1995 |
| EP | 0 732 334 | 9/1996 |
| EP | 1462103 | 9/2004 |
| EP | 2 239 264 | 10/2010 |
| EP | 2415767 | 2/2012 |
| EP | 2568287 | 3/2013 |
| EP | 2573559 | 3/2013 |
| FR | 2747678 | 10/1997 |
| JP | H 03014566 | 1/1991 |
| JP | H 05-097849 | 4/1993 |
| JP | 08-269058 | 10/1996 |
| JP | 2004-502650 | 1/2004 |
| JP | 2006-509764 | 3/2006 |
| JP | 2008-532954 | 8/2008 |
| JP | 2009-503069 | 1/2009 |
| JP | 2012-529536 | 11/2012 |
| JP | 2012-530053 | 11/2012 |
| JP | 2013/010719 | 1/2013 |
| JP | 2016-520062 | 7/2016 |
| JP | 2016-522246 | 7/2016 |
| JP | 6243003 | 12/2017 |
| JP | 6529546 | 6/2019 |
| KR | 20150037711 | 4/2015 |
| WO | WO 2002/000196 | 1/2002 |
| WO | WO 2004/024736 | 3/2004 |
| WO | WO 2005/080334 | 1/2005 |
| WO | WO 2005/099688 | 10/2005 |
| WO | WO 2006/124874 | 11/2006 |
| WO | WO 2007/018998 | 2/2007 |
| WO | WO 2008/154221 | 12/2008 |
| WO | WO 2009/020559 | 2/2009 |
| WO | WO 2009/020677 | 2/2009 |
| WO | WO 2009/084693 | 7/2009 |
| WO | WO 2010/046190 | 4/2010 |
| WO | WO 2010/144679 | 12/2010 |
| WO | WO 2010/144680 | 12/2010 |
| WO | WO 2011/024987 | 3/2011 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/054851 | 5/2011 |
| WO | WO 2011/133722 | 10/2011 |
| WO | WO 2011/143651 | 11/2011 |
| WO | WO 2011/143657 | 11/2011 |
| WO | WO 2011/143660 | 11/2011 |
| WO | WO 2011/143669 | 11/2011 |
| WO | WO 2011/161031 | 12/2011 |
| WO | WO 2012/075383 | 6/2012 |
| WO | WO 2012/075456 | 6/2012 |
| WO | WO 2012/107465 | 8/2012 |
| WO | WO 2012/116170 | 8/2012 |
| WO | WO 2012/143413 | 10/2012 |
| WO | WO 2012/143415 | 10/2012 |
| WO | WO 2012/143416 | 10/2012 |
| WO | WO 2012/150234 | 11/2012 |
| WO | WO 2012/151512 | 11/2012 |
| WO | WO 2012/174487 | 12/2012 |
| WO | WO 2012/178208 | 12/2012 |
| WO | WO 2013/019710 | 2/2013 |
| WO | WO 2013/024104 | 2/2013 |
| WO | WO 2013/027168 | 2/2013 |
| WO | WO 2013/029548 | 3/2013 |
| WO | WO 2013/030150 | 3/2013 |
| WO | WO 2013/033268 | 3/2013 |
| WO | WO 2013/033269 | 3/2013 |
| WO | WO 2013/033270 | 3/2013 |
| WO | WO 2013/043553 | 3/2013 |
| WO | WO 2013/044511 | 4/2013 |
| WO | WO 2013/064900 | 5/2013 |
| WO | WO 2013/097052 | 7/2013 |
| WO | WO 2013/097601 | 7/2013 |
| WO | WO 2013/148197 | 10/2013 |
| WO | WO 2013/155695 | 10/2013 |
| WO | WO 2013/156869 | 10/2013 |
| WO | WO 2013/158952 | 10/2013 |
| WO | WO 2013/175281 | 11/2013 |
| WO | WO 2013/184876 | 12/2013 |
| WO | WO 2013/184878 | 12/2013 |
| WO | WO 2013/185284 | 12/2013 |
| WO | WO 2013/186612 | 12/2013 |
| WO | WO 2013/188381 | 12/2013 |
| WO | WO 2014/001356 | 1/2014 |

(56) References Cited

FOREIGN PATENT DOCUMENTS

| | | |
|---|---|---|
| WO | WO 2014/015175 | 1/2014 |
| WO | WO 2014/026997 | 2/2014 |
| WO | WO 2014/028547 | 2/2014 |
| WO | WO 2014/048945 | 4/2014 |
| WO | WO 2014/068402 | 5/2014 |
| WO | WO 2014/076146 | 5/2014 |
| WO | WO 2014/078257 | 5/2014 |
| WO | WO 2014/080290 | 5/2014 |
| WO | WO 2014/080291 | 5/2014 |
| WO | WO 2014/095774 | 6/2014 |
| WO | WO 2014/095775 | 6/2014 |
| WO | WO 2014/096965 | 6/2014 |
| WO | WO 2014/128655 | 8/2014 |
| WO | WO 2014/134232 | 9/2014 |
| WO | WO 2014/134267 | 9/2014 |
| WO | WO 2014/139324 | 9/2014 |
| WO | WO 2014/140076 | 9/2014 |
| WO | WO 2014/140077 | 9/2014 |
| WO | WO 2014/143768 | 9/2014 |
| WO | WO 2014/145051 | 9/2014 |
| WO | WO 2014/152029 | 9/2014 |
| WO | WO 2014/154760 | 10/2014 |
| WO | WO 2014/154762 | 10/2014 |
| WO | WO 2014/159392 | 10/2014 |
| WO | WO 2014/159837 | 10/2014 |
| WO | WO 2014/160873 | 10/2014 |
| WO | WO 2014/164596 | 10/2014 |
| WO | WO 2014/164771 | 10/2014 |
| WO | WO 2014/164780 | 10/2014 |
| WO | WO 2014/165127 | 10/2014 |
| WO | WO 2014/165143 | 10/2014 |
| WO | WO 2014/170350 | 10/2014 |
| WO | WO 2014/173241 | 10/2014 |
| WO | WO 2014/182929 | 11/2014 |
| WO | WO 2014/191894 | 12/2014 |
| WO | WO 2014/191896 | 12/2014 |
| WO | WO 2014/191906 | 12/2014 |
| WO | WO 2014/191911 | 12/2014 |
| WO | WO 2014/202578 | 12/2014 |
| WO | WO 2014/206150 | 12/2014 |
| WO | WO 2014/206345 | 12/2014 |
| WO | WO 2014/210425 | 12/2014 |
| WO | WO 2015/002754 | 1/2015 |
| WO | WO 2015/004533 | 1/2015 |
| WO | WO 2015/004534 | 1/2015 |
| WO | WO 2015/006193 | 1/2015 |
| WO | WO 2015/007711 | 1/2015 |
| WO | WO 2015/013635 | 1/2015 |
| WO | WO 2015/081203 | 6/2015 |
| WO | WO 2015/095445 | 6/2015 |
| WO | WO 2015/162169 | 10/2015 |
| WO | WO 2015/163485 | 10/2015 |
| WO | WO 2015/164480 | 10/2015 |
| WO | WO 2015/168555 | 11/2015 |
| WO | WO 2015/168621 | 11/2015 |
| WO | WO 2015/169951 | 11/2015 |
| WO | WO 2015/169953 | 11/2015 |
| WO | WO 2015/184257 | 12/2015 |
| WO | WO 2016/044130 | 3/2016 |
| WO | WO 2017/127930 | 3/2016 |
| WO | WO 2016/077378 | 5/2016 |
| WO | WO 2016/186453 | 11/2016 |
| WO | WO 2016/194806 | 12/2016 |
| WO | WO 2017/133681 | 8/2017 |
| WO | WO 2018/086604 | 5/2018 |

OTHER PUBLICATIONS

Australian Office Action in Australian Application No. 2014228175, dated May 10, 2018, 4 pages.
Australian Office Action in Australian Application No. 2015249810, dated Aug. 21, 2018, 4 pages.
Argentina Office Action in Argentina Application No. 2014/0101029, dated Dec. 2, 2019, 6 pages.
Bamborough et al., "Fragment-Based Discovery of Bromodomain Inhibitors Part 2: Optimization of Phenylisoxazole Sulfonamides," J Med Chem., 2012, 55:587-596.
Bartholomeeusen et al., "BET bromodomain inhibition activates transcription via a transient release of P-TEFb from 7SK snRNP," JBC, 2012, 16 pages.
Bauer, "Pharmaceutical Solids—the Amorphous Phase," Journal of Validation Technology, Jan. 2009, 15(3): 63-68.
Belkina and Denis, "BET domain co-regulators in obesity inflammation and cancer," Nat Rev Cancer, Jul. 2012, 12:465-477.
Belkina et al., "BET Protein Function is Required for Inflammation: Brd2 Genetic Disruption and BET Inhibitor JQ1 Impair Mouse Macrophage Inflammatory Responses," J Immunol., 2013, 190:3670-3678.
Berge et al., "Pharmaceutical Salts," J Pharm. Sci., 1977, 66(1):1-19.
Blom et al., "Optimizing Preparative LC-MS Configurations and Methods for Parallel Synthesis Purification," J Comb Chem., 2003, 5(5):670-683.
Blom et al., "Preparative LCMS Purification: Improved Compound Specific Method Optimization," J Comb Chem., 2004, 6(6):874-883.
Blom, "Two-pump at-column-dilution configuration for preparative liquid chromatography-mass spectrometry," J Comb Chem., 2002, 4(4):295-301.
Brazilian Office Action in Brazilian Application No. BR112015022942-5, dated Nov. 28, 2019, 5 pages.
Byrn et al., "Pharmaceutical Solids: A Strategic Approach to Regulatory Considerations," Pharmaceutical Research, Jul. 1995, 12(7): 945-954.
Caira, "Crystalline Polymorphism of Organic Compounds," Topics in Current Chemistry, 1998, 198: 163-208.
Cheng et al., "Inhibition of BET Bromodomain Targets Genetically Diverse Glioblastoma," Clin Cancer Res 19:1748-1759, Feb. 2013.
Chiang, "Brd4 engagement from chromatin targeting to transcriptional regulation: selective contact with acetylated histone H3 and H4," Biology Reports, Dec. 2009, 1:98, 7 pages.
Chilean Office Action in Chilean Application No. 201502734, dated Jan. 18, 2017, 8 pages (English Translation).
Chilean Office Action in Chilean Application No. 2016-002681, dated Jul. 19, 2018, 9 pages.
Chilean Office Action in Chilean Application No. 2734-2015, dated Apr. 1, 2019, 4 pages.
Chilean Office Action in Chilean Application No. 3702-2018, dated Nov. 15, 2019, 22 pages.
Chinese Office Action in Chinese Application No. 201480025137, dated Feb. 16, 2017, 21 pages (w/ English Translation).
Chinese Office Action in Chinese Application No. 201480025137, dated May 17, 2016, 14 pages (English Translation).
Chinese Office Action in Chinese Application No. 201480025137, dated Oct. 13, 2017, 7 pages (English Translation).
Chung et al., "Discovery and Characterization of Small Molecule Inhibitors of the BET Family Bromodomains," J Med Chem., 2011, 54:3827-3838.
Chung et al., "Fragment-based discovery of bromodomain inhibitors part 1: inhibitor binding modes and implications for lead discovery," J Med Chem,. 2011, 6 pages.
Chung et al., "Fragment-based discovery of bromodomain inhibitors part 1: inhibitor binding modes and implications for lead discovery," Supporting Information, 2011, 6 pages.
Colombian Office Action in Colombian Application No. 15-227.987, dated May 23, 2017, 5 pages.
Colombian Office Action in Colombian Application No. NC2018/0008205, dated Jun. 18, 2019, 7 pages.
Colombian Office Action in Colombian Application No. NC2016/0003978, dated Jul. 16, 2018, 4 pages.
Costa Rican Office Action in Costa Rican Application No. 2015-513, dated Aug. 5, 2019, 14 pages.
Dawson et al., "Inhibition of BET recruitment to chromatin as an effective treatment for MLL-fusion leukaemia," Nature, 2011, 5 pages.

(56) References Cited

OTHER PUBLICATIONS

Dawson, "Supplementary Information: Inhibition of BET recruitment to chromatin as an effective treatment for MLL-fusion leukaemia," Nature, 2011, 50 pages.
Delmore et al., "BET bromodomain inhibition as a therapeutic strategy to target c-Myc," Cell, 2011, 146(6):904-917, Supplemental Information: S1-S11.
Delmore et al., "BET bromodomain inhibition as a therapeutic strategy to target c-Myc," Cell, Sep. 2011, 146(6):904-917.
Devaiah et al., "BRD4 is an atypical kinase that phosphorylates serine2 of the RNA polymerase II carboxy-terminal domain," Proc. Nat. Acad. Sci. USA., 2012, 109(18):6927-6932.
Doroshow et al., "BET inhibitors: a novel epigenetic approach," Ann Oncol., Aug. 1, 2017, 28(8):1776-1787.
Dorwald, F. Zaragoza. Side Reactions in Organic Synthesis: A Guide to Successful Synthesis Design, Weinheim: Wiley-VCH Verlag GmbH & Co. KGaA, 2005, Preface.
Draker et al., "A Combination of H2A.Z and H4 Acetylation Recruits Brd2 to Chromatin during Transcriptional Activation," PLoS Genet., Nov. 2012, 8(11):e1003047, 17 pages.
Ecuador Opposition in Ecuador Application No. 2019-1982, dated Oct. 10, 2019, 33 pages.
European Extended Search Report in European Application No. 19189853.5, dated Aug. 30, 2019, 8 pages.
Eurasian Office Action in Eurasian Application No. 201692134, dated Jun. 6, 2017, 4 pages (English Translation).
Eurasian Office Action in Eurasian Application No. 201692134, dated Feb. 21, 2019, 4 pages.
Eurasian Office Action in Eurasian Application No. 201591785, dated Apr. 4, 2019, 4 pages.
Eurasian Office Action in Eurasian Application No. 201692134, Jun. 21, 2019, 2 pages.
Filippakopoulos and Knapp, "Targeting bromodomains: epigenetic readers of lysine acetylation," Nature Rev Drug Disc., May 2014, 13:337-356.
Filippakopoulos et al., "Benzodiazepines and benzotriazepines as protein interaction inhibitors targeting bromodomains of the BET family," Bioorg Med Chem., 2011, 9 pages.
Filippakopoulos et al., "Histone Recognition and Large-Scale Structural Analysis of the Human Bromodomain Family," Cell, Mar. 2012, 149:214-231.
Filippakopoulos et al., "Selective inhibition of BET bromodomains," Nature, 2010, 468:1067-1073.
Filippakopoulos et al., "Supplemental Information: Selective inhibition of BET bromodomains," Nature, 2010, 468:1067-1073.
Floyd et al., "Supplemental Information: The bromodomain protein Brd4 insulates chromatin from DNA damage signalling," Nature, 2013, 14 pages.
Floyd et al., "The bromodomain protein Brd4 insulates chromatin from DNA damage signalling," Nature, 2013, 498:246-250.
French et al., "BRD4-NUT fusion oncogene: a novel mechanism in aggressive carcinoma," Cancer Res., 2003, 63(2):304-307.
French et al., "BRD-NUT oncoproteins: a family of closely related nuclear proteins that block epithelial differentiation and maintain the growth of carcinoma cells," Oncogene, 2008, 27:2237-2242.
French et al., "Midline carcinoma of children and young adults with NUT rearrangement," J Clin. Oneal., 2004, 22(20):4135-4139.
French, "Demystified molecular pathology of NUT midline carcinomas," J Clin Pathol., 2010, 63:492-496.
French, "NUT midline carcinoma," Cancer Genet Cytogenetics, 2010, 203:16-20.
Frizzo et al., "Structural and thermodynamic properties of new pyrazolo [3,4-d] pyridazinones," Thermochimica Acta., Oct. 2013, 574:63-72.
Gallenkamp et al., "Bromodomains and their Pharmacological Inhibitors," Chem Med Chem., Mar. 2014, 9(3):438-464.
Gamier et al., "BET bromodoma in inhibitors: a patent review," Exp Opin Therapeutic Patents, Feb. 2014, 24(2):185-199.
Greenwald et al., "E-BRD2 transgenic mice develop B-cell lymphoma and leukemia," Blood 103(4):1475-1484, Feb. 2004.
Hackam et al., JAMA, 296(14), 2006, 1731-1732.
Hewings et al., "3,5-Dimethylisoxazoles Act as Acetyl-lysine-mimetic Bromodomain Ligands," J Med Chem., 2011, 54:6761-6770.
Hewings et al., "Progress in the Development and Applciation of Small Molecule Inhibitors of Bromodomain-Acetyl-lysine Interactions," J Med Chem., Nov. 2012, 104 pages (Author Manuscript).
Houzelstein et al., "Growth and Early Postimplantation Defects in Mice Deficient for the Bromodomain-Containing Protein Brd4," Mole Cell Biol., Jun. 2002, 22(11):3794-3802.
Huang et al., "Brd4 coactivates transcriptional activation of NF-κB via specific binding to acetylated RelA," Mol. Cell Biol., 2009, 29(5):1375-1387.
Indian Office Action in Indian Application No. 201617038915, dated Jul. 11, 2019, 6 pages.
Indian Office Action in Indian Application No. 9464/DELNP/2015, dated Oct. 23, 2019, 7 pages.
Indonesian Office Action P-00201506648, dated May 7, 2018, 5 pages (english translation).
Indonesian Office Action in Indonesian Application No. P00201607912, dated Dec. 9, 2019, 4 pages.
International Preliminary Report on Patentability in International Application No. PCT/US2014/027872, dated Sep. 24, 2015, 8 pages.
International Preliminary Report on Patentability in International Application No. PCT/US2014/045543, dated Jan. 21, 2016, 7 pages.
International Preliminary Report on Patentability in International Application No. PCT/US2014/067598, dated May 31, 2016, 7 pages.
International Preliminary Report on Patentability in International Application No. PCT/US2014/067629, dated May 31, 2016, 7 pages.
International Preliminary Report on Patentability in International Application No. PCT/US2014/067691, dated May 31, 2016, 7 pages.
International Preliminary Report on Patentability in International Application No. PCT/US2014/071102, dated Jun. 21, 2016, 7 pages.
International Preliminary Report on Patentability in International Application No. PCT/US2015/027047, dated Oct. 25, 2016, 10 pages.
International Preliminary Report on Patentability in International Application No. PCT/US2017/038121, dated Dec. 25, 2018, 10 pages.
International Search Report and Written Opinion in International Application No. PCT/US2014/027872, dated Jun. 30, 2014, 12 pages.
International Search Report and Written Opinion in International Application No. PCT/US2014/045543, dated Sep. 10, 2014, 11 pages.
International Search Report and Written Opinion in International Application No. PCT/US2014/067598, dated Feb. 13, 2015, 9 pages.
International Search Report and Written Opinion in International Application No. PCT/US2014/067629, dated Feb. 16, 2015, 11 pages.
International Search Report and Written Opinion in International Application No. PCT/US2014/067691, dated Feb. 2, 2015, 10 pages.
International Search Report and Written Opinion in International Application No. PCT/US2014/071102, dated Feb. 13, 2015, 9 pages.
International Search Report and Written Opinion in International Application No. PCT/US2015/027047, dated Jul. 10, 2015, 14 pages.
International Search Report and Written Opinion in International Application No. PCT/US2015/049909, dated Dec. 7, 2015, 13 pages.
International Search Report and Written Opinion in International Application No. PCT/US2016/059360, dated Feb. 13, 2017, 20 pages.

(56) References Cited

OTHER PUBLICATIONS

International Search Report and Written Opinion in International Application No. PCT/US2017/038121, dated Oct. 20, 2017, 20 pages.
Israeli Office Action in Israeli Application No. 248,415, dated Jan. 31, 2019, 7 pages.
Jang et al., "The bromodomain protein Brd4 is a positive regulatory component of P-TEFb and stimulates RNA polymerase II-dependent transcription," Mol. Cell, Aug. 2005, 19(4):523-534.
Japanese Office Action in Japanese Application No. 2016-502650, dated Jan. 10, 2017, 3 pages (English translation only).
Japanese Office Action in Japanese Application No. 2017-134538, dated Jun. 12, 2018, 7 pages (English Translation).
Japanese Office Action in Japanese Application No. 2016-525398, dated May 15, 2018, 5 pages (English Translation).
Japanese Office Action in Japanese Application No. 2016-563976, dated Nov. 20, 2018, 9 pages.
Japanese Office Action in Japanese Application No. 2017-514515, dated Jun. 4, 2019, 6 pages.
Jin et al., "c-Myb binds MLL through menin in human leukemia cells and is an important driver of MLL-associated leukemogenesis," J Clinc Invest., 2010, 120(2):593-606.
Jordan, V.C. Nature Reviews: Drug Discovery, 2, 2003, 205.
Jung et al., "Affinity Map of BRD4 Interactions with the Histone H4 Tail and the Small Molecule Inhibitor JQ1," J Biol Chem., 2014, 28 pages.
Lamonica et al., "Bromodomain protein Brd3 associates with acetylated GATA1 to promote its chromatin occupancy at erythroid target genes," Proc. Nat. Acad. Sci., USA, 2011, 108(22):E159-168.
Leroy et al., "The double bromodomain proteins Brd2 and Brd3 couple histone acetylation to transcription," Mol. Cell, Apr. 2008, 30(1):51-60.
Lockwood et al., "Sensitivity of human lung adenocarcinoma cell lines to targeted inhibition of BET epigenetic signaling proteins," PNAS Early Edition, 2012, 14 pages.
Malaysian Office Action in Malaysian Application No. PI2015002162, dated Jul. 25, 2019, 3 pages.
Martin et al., "Cyclin-Dependent Kinase Inhibitor Dinaciclib Interacts with the Acetyl-Lysine Recognition Site of Bromodomains," ACS Chem Biol., 2013, 8:2360-2365.
Maruyama et al., "A Mammalian Bromodomain Protein, Brd4, Interacts with Replication Factor C and Inhibits Progression to S Phase," Mol Cell Biol., 2002, 22(18):6509-6520.
Matzuk et al., "Small-Molecule Inhibition of BRDT for Male Contraception," Cell, Aug. 2012, 150:673-684.
McLure et al., "RVX-208, an Inducer of ApoA-I in Humans, is a BET Bromodomain Antagonist," PLOS One, Dec. 2013, 8(12):e83190, 12 pages.
Mertz et al., "Targeting MYC dependence in cancer by inhibiting BET bromodomains," PNAS, 2011, 108(40):16669-16674.
Mexican Office Action in Mexican Application No. MX/a/2015/013149, dated Sep. 10, 2018, 5 pages.
Mexican Office Action in Mexican Application No. MX/a/2015/013149, dated Mar. 15, 2019, 2 pages.
Mexican Office Action in Mexican Application No. MX/a/2016/013851, dated Jul. 16, 2019, 5 pages.
Mexican Office Action in Mexican Application No. MX/a/2016/013851, dated Nov. 22, 2019, 5 pages.
Mirguet et al., "From ApoA1 upregulation to BET family bromodomain inhibition: Discovery of I-BET151," Bioorg Med Chem Lett., 2012, 22:2963-2967.
Mochizuki et al., "The bromodomain protein Brd4 stimulates G1 gene transcription and promotes progression to S phase," J Biol. Chem. 2008, 283(14):9040-9048.
Moriniere et al., "Cooperative binding of two acetylation marks on a histone tail by a single bromodomain," Nature, 2009, 461:664-669.
Muller et al., "Bromodomains as therapeutic targets," Expert Reviews, 2011, 13:e29, 21 pages.
New Zealand Office Action in New Zealand Application No. 712453, dated Sep. 13, 2019, 4 pages.
Nicodeme et al., "Supplementary Information: Suppression of inflammation by a synthetic histone mimic," Nature, 2010, 40 pages.
Nicodeme et al., "Suppression of inflammation by a synthetic histone mimic," Nature, 2010, 468:1119-1123.
Nishiyama et al., "Brd4 is Required for Recovery from Antimicrotubule Drug-induced Mitotic Arrest: Preservation of Acetylated Chromatin," Mol Biol Cell, Feb. 2006, 17:814-823.
Ott et al., "BET bromodomain inhibition targets both c-MYC and IL7R in high-risk acute lymphoblastic leukemia," Blood, published online 2012, 29 pages.
Peturssion et al., "Protecting Groups in Carbohydrate Chemistry," J Chem. Educ., 1997, 74(11):1297-1303.
Peruvian Office Action in Peruvian Application No. 2021.15, dated Sep. 24, 2019, 21 pages.
Philippian Office Action in Philippian application No. 1/2016/502115, dated Sep. 6, 2018, 4 pages.
Philippian Office Action in Philippian Application No. 1/2016/502115, dated Nov. 5, 2019, 3 pages.
Picaud et al., "RVX-208, an inhibitor of BET transcriptional regulators with selectivity for the second bromodomain," PNAS Early Edition, 2013, 6 pages.
Picaud et al., "Supplemental Information: RVX-208, an inhibitor of BET transcriptional regulators with selectivity for the second bromodomain," PNAS Early Edition, 2013, 9 pages.
Prinjhas et al., "Place your BETs: the therapeutic potential of bromodomains," Trends Pharmacol Sci., 2012, 33(3):146-153.
Puissant et al., "Targeting MYCN in Neuroblastoma by BET Bromodomain Inhibition," Cancer Discovery, 16 pages, Mar. 2013.
Rahman et al., "The Brd4 Extraterminal Domain Confers Transcription Activation Independent of pTEFb by Recruiting Multiple Proteins, Including NSD3," Mol Cell Biol., Jul. 2011, 31(13):2641-2652.
Ravin, "Preformulation," Remington's Pharmaceutical Sciences, 17th Ed., (Mack Publishing Company, Easton, 1985), pp. 1409-1423.
Sanchez and Zhou, "The role of human bromodomains in chromatin biology and gene transcription," Curr Opin Drug Discov Devel., Sep. 2009, 12(5):659-665 (Author Manuscript).
Schroder et al., "Two-pronged Binding with Bromodomain-containing Protein 4 Liberates Positive Transcription Elongation Factor b from Inactive Ribonucleoprotein Complexes," J Biol Chem., Jan. 6, 2012, 287(2):1000-1009.
Schwartz et al., "Differentiation of NUT Midline Carcinoma by Epigenomic Reprogramming," Cancer Res., 2011, 71:2686-2696.
Seal et al., "Identification of a novel series of BET family bromodomain inhibitors: Binding mode and profile of I-BET151 (GSK1210151A)," Bioorg Med Chem., 2012, 22:2968-2972.
Segura et al., "BRD4 Sustains Melanoma Proliferation and Represents a New Target for Epigenetic Therapy," Cancer Res 73:6264-6276, Aug. 2013.
Shimamum et al., "Efficacy of BET Bromodomain Inhibition in Kras-Mutant Non-Small Cell Lung Cancer," Clin Cancer Res, 10 pages, 2013.
Smith et al., "Genome-wide siRNA screen identifies SMCX, EP400, and Brd4 as E2-dependent regulators of human papillomavirus oncogene expression," PNAS, Feb. 23, 2010, 107(8):3752-3757.
Sri Lanka Office Action in Sri Lanka Application No. 18419, dated Nov. 27, 2019, 1 page.
Stenman et al., "New tricks from an old oncogene: Gene fusion and copy number alterations of MYB in human cancer," Cell Cyle, Aug. 2010, 9(15):2986-2955.
Taiwan Office Action in Taiwan application No. 103109291, dated Oct. 9, 2018, 6 pages.
Taiwan Office Action in Taiwan application No. 104112916, dated Feb. 23, 2019, 7 pages.
Taiwan Office Action in Taiwan Application No. 104130337, dated Jul. 31, 2019, 7 pages.
Ukrainian Office Action in Ukrainian Application No. A201510087, dated Aug. 9, 2018, 10 pages.

(56) References Cited

OTHER PUBLICATIONS

Vidler et al., "Druggability Analysis and Structural Classification of Bromodomain Acetyl-lysine Binding Sites," J Med Chem., 2012, 14 pages.

Vietnamese Office Action in Vietnamese Office Application No. 1-2015-03963, dated Apr. 22, 2019, 4 pages.

Vietnamese Office Action in Vietnamese Office Application No. 1-2016-04470, dated Oct. 25, 2019, 4 pages.

Wang et al., "Brd2 disruption in mice causes severe obesity without Type 2 diabetes," Biochem. J., 2010, 425(1):71-83.

Wang et al., "The Bromodomain Protein Brd4 Associated with Acetylated Chromatin is Important for Maintenance of Higher-Order Chromatin Structure," JBC, 2012, 22 pages.

Weidner-Glunde et al., "What do viruses BET on?" Frontiers Biosci., Jan. 2010, 15:537-549.

Wu and Chiang et al., "The Double Bromodomaincontaining Chromatin Adaptor Brd4 and Transcriptional Regulation," J Biol Chem., May 2007, 282(18):13141-13145.

Wu et al., "Brd4 links chromatin targeting to HPV transcriptional silencing," Genes Dev., 2006, 20:2383-2396.

Wyce et al "Inhibition of BET bromodomain proteins as a therapeutic appraoch in prostate cancer," Oncotarget, 13 pages, Nov. 2013.

Yan et al., "Perturbation of BRD4 Protein Function by BRD4-NUT Protein Abrogates Cellular Differentiation in NUT Midline Carcinoma," J Biol Chem., Aug. 2011, 286(31):27663-27675.

Yan et al., "Supplemental Data: Perturbation of BRD4 Protein Function by BRD4-NUT Protein Abrogates Cellular Differentiation in NUT Midline Carcinoma," J Biol Chem., Aug. 2011, 12 pages.

Yang et al., "Brd4 Recruits P-TEFb to Chromosomes at Late Mitosis to Promote G1 Gene Expression and Cell Cycle Progression," Mol Cell Biol., Feb. 2008, 28(3):967-976.

You et al., "Interaction of the bovine papillomavirus E2 protein with Brd4 tethers the viral DNA to host mitotic chromosomes," Cell, 2004, 117(3):349-60.

You et al., "Regulation of Aurora B Expression by the Bromodomain Protein Brd4," Mol Cell Biol., Sep. 2009, 29(18):5094-5103.

Zhang et al., "Bromodomain-Containing-Protein 4 (BRD4) Regulates RNA Polymerase II Serine 2 Phosphorylation in Human CD4+ T Cells," JBC, 2012, 30 pages.

Zhu et al., "Reactivation of latent HIV-1 by inhibition of BRD4," Cell Reports, 2012, 2(4):807-816.

Zuber et al., "An integrated approach to dissecting oncogene addiction implicates a Myb-coordinated self-renewal program as essential for leukemia maintenance," Genes Dev., 2011, 25:1628-1640.

Zuber et al., "RNAi screen identifies Brd4 as a therapeutic target in acute myeloid leukaemia," Nature, 2011, 478(7370):524-528.

Zuber et al., "Supplemental Information: RNAi screen identifies Brd4 as a therapeutic target in acute myeloid leukaemia," Nature, 2011, 33 pages.

AMORPHOUS SOLID FORM OF A BET PROTEIN INHIBITOR

FIELD OF THE INVENTION

The present invention relates to an amorphous solid form of (4S)-7-(3,5-dimethylisoxazol-4-yl)-4-pyridin-2-yl-4,5-dihydroimidazo[1,5,4-de][1,4]benzoxazin-2(1H)-one, and processes for its preparation, which is an inhibitor of BET proteins such as BRD2, BRD3, BRD4, and BRD-t and is useful in the treatment of various diseases such as cancer.

BACKGROUND OF THE INVENTION

The BET (Bromodomain and Extra-Terminal) family of bromodomain containing proteins comprises 4 proteins (BRD2, BRD3, BRD4 and BRD-t) that share a conserved structural organization containing tandem N-terminal bromodomains capable of binding to acetylated lysine residues of histones and other proteins. BRD2, BRD3 and BRD4 are ubiquitously expressed while BRD-t is restricted to germ cells. BRD proteins play essential, but non-overlapping roles in regulating gene transcription and controlling cell growth. BET proteins are associated with large protein complexes including Mediator, PAFc and super elongation complex that regulate many aspects of gene transcription. BRD2 and BRD4 proteins have been shown to remain in complex with chromosomes during mitosis and are required to promote transcription of critical genes including cyclin D and c-Myc that initiate the cell cycle. Mochizuki et al., *J. Biol. Chem.* 2008, 283, 9040-9048. BRD4 is essential for recruiting the protein translational elongation factor B complex to the promoters of inducible genes resulting in the phosphorylation of RNA polymerase II and stimulating productive gene transcription and elongation. Jang et al., *Mol. Cell,* 2005, 19, 523-534. In some instances, a kinase activity of BRD4 may directly phosphorylate and activate RNA polymerase II. Devaiah et al., *Proc. Nat. Acad. Sci., USA.* 2012, 109, 6927-6932. Cells lacking BRD4 show impaired progression through cell cycle. BRD2 and BRD3 are reported to associate with histones along actively transcribed genes and may be involved in facilitating transcriptional elongation. Leroy et al., *Mol. Cell,* 2008, 30, 51-60. In addition to acetylated histones, BET proteins have been shown to bind selectively to acetylated transcription factors including the RelA subunit of NF-kB and GATA1 thereby directly regulating the transcriptional activity of these proteins to control expression of genes involved in inflammation and hematopoietic differentiation. Huang et al., *Mol. Cell Biol.,* 2009, 29, 1375-1387; Lamonica et al., *Proc. Nat. Acad. Sci., USA,* 2011, 108, E159-168.

A recurrent translocation involving NUT (nuclear protein in testes) with BRD3 or BRD4 to form a novel fusion oncogene, BRD-NUT, is found in a highly malignant form of epithelial neoplasia. French et al., *Cancer Res.,* 2003, 63, 304-307; French et al., *J. Clin. Oncol.,* 2004, 22, 4135-4139. Selective ablation of this oncogene restores normal cellular differentiation and reverses the tumorigenic phenotype. Filippakopoulos et al., *Nature,* 2010, 468, 1068-1073. Genetic knockdown of BRD2, BRD3 and BRD4 has been shown to impair the growth and viability of a wide range of hematological and solid tumor cells. Zuber et al., *Nature,* 2011, 478, 524-528; Delmore et al., *Cell,* 2011, 146, 904-917. Aside from a role in cancer, BET proteins regulate inflammatory responses to bacterial challenge, and a BRD2 hypomorph mouse model showed dramatically lower levels of inflammatory cytokines and protection from obesity induced diabetes. Wang et al., *Biochem. J.,* 2009, 425, 71-83; Belkina et al., *J. Immunol.* 102838, online publication before print, Feb. 18, 2013. In addition, some viruses make use of these BET proteins to tether their genomes to the host cell chromatin, as part of the process of viral replication or use BET proteins to facilitate viral gene transcription and repression. You et al., *Cell,* 2004, 117, 349-60; Zhu et al., *Cell Reports,* 2012, 2, 807-816.

Inhibitors of BET proteins are in current development. Exemplary BET protein inhibitors are disclosed in, for example, U.S. Pat. App. Pub. Nos. 2014/0275030; 2015/0011540; 2015/0148375; 2015/0148342; 2015/0148372; and 2015/0175604. An example of BET protein inhibitor is (4S)-7-(3,5-dimethylisoxazol-4-yl)-4-pyridin-2-yl-4,5-dihydroimidazo[1,5,4-de][1,4]benzoxazin-2(1H)-one which is described in U.S. Pat. App. Pub. No. 2014/0275030. While certain inhibitors of BET proteins are in the literature, there remains a need for new solid forms of these inhibitors having suitable properties useful in the manufacture of safe, effective, high quality drug products. The present invention described herein is directed toward this end.

SUMMARY OF THE INVENTION

The present invention provides, inter alia, a solid form, which is an amorphous powder, of the BET protein-inhibiting compound (4S)-7-(3,5-dimethylisoxazol-4-yl)-4-pyridin-2-yl-4,5-dihydroimidazo[1,5,4-de][1,4]benzoxazin-2(1H)-one, compositions, methods of use, and methods for preparing the same.

The present invention also provides intermediate compounds generated during the preparation of (4S)-7-(3,5-dimethylisoxazol-4-yl)-4-pyridin-2-yl-4,5-dihydroimidazo[1,5,4-de][1,4]benzoxazin-2(1H)-one and methods for preparing these intermediate compounds.

The details of one or more embodiments are set forth in the description below. Other features, objects, and advantages will be apparent from the description and from the claims.

DETAILED DESCRIPTION

Solid Form

The present invention provides, inter alia, a solid form, which is an amorphous solid, of the BET protein-inhibiting compound (4S)-7-(3,5-dimethylisoxazol-4-yl)-4-pyridin-2-yl-4,5-dihydroimidazo[1,5,4-de][1,4]benzoxazin-2(1H)-one (see below), referred to herein as "Compound 1-(S)." In one embodiment, the solid is an amorphous powder. An alternative name for the same compound is (3S)-6-(3,5-dimethylisoxazol-4-yl)-3-(pyridin-2-yl)-3,4-dihydro-5-oxa-1,2a-diazaacenaphthylen-2(1H)-one.

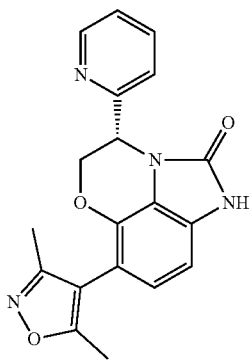

Compound 1-(S)

The amorphous solid form of the invention has several properties making it particularly suitable for scale up and formulation. For example, the solid form of the invention has good stability with respect to decomposition and unwanted conversion to crystalline forms as evidenced by stability studies (see Example 5) and a relatively high glass transition temperature (see Example 4). Additionally, the amorphous solid form can be reliably prepared in high purity, with little to no unwanted residual organic solvent. Residual organic solvent can include any solvents that were employed during the synthesis of the solid form, or residues or impurities present in the starting materials and reagents.

Figure 1:
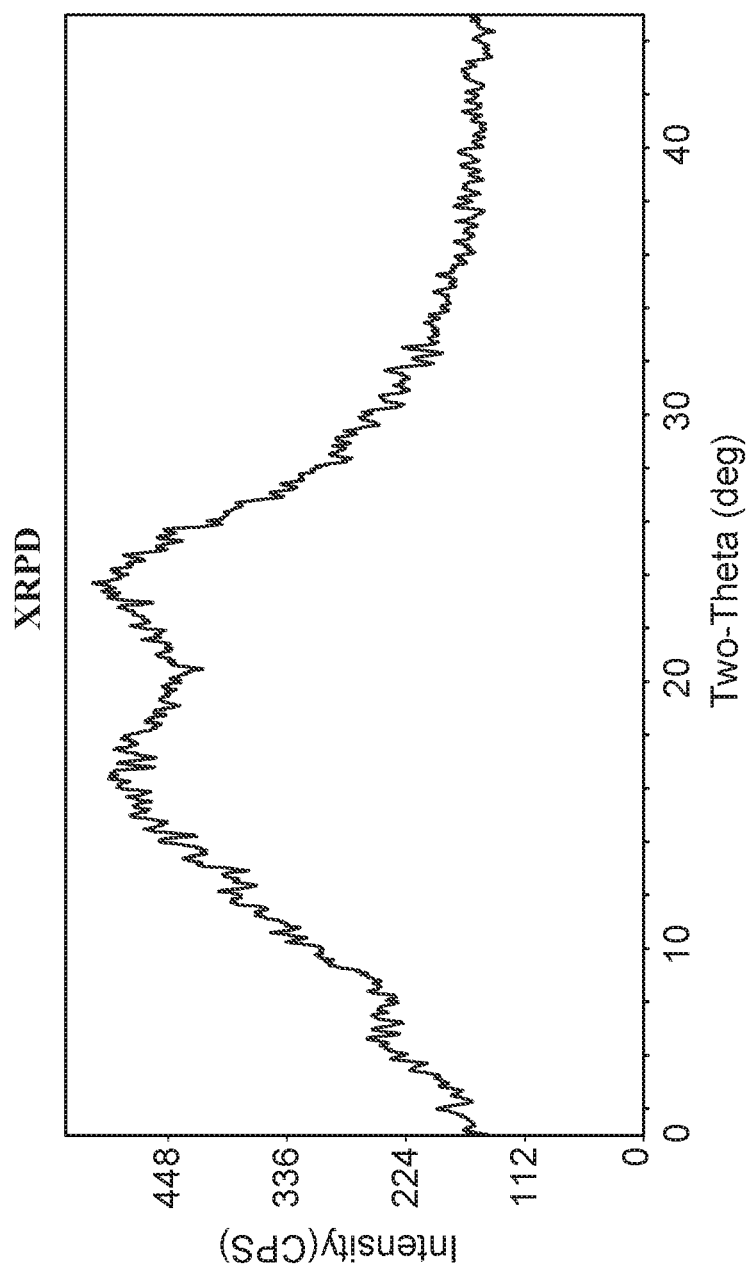
FIG. 1 shows an XRPD pattern for Compound 1-(S) amorphous powder.

In some embodiments, the solid form of the invention is characterized by an XRPD (X-ray power diffraction) pattern substantially as shown in FIG. 1. As can be seen in the XRPD pattern, no reflections are observed, indicating a homogenous amorphous solid form. The XRPD is obtained from powder diffractometer with X-ray radiation from copper at 1.054056 Å with $K_\beta$ filter and X-ray power at 30 KV, 15 mA, and the sample powder was dispersed on a zero-background sample holder (see Example 2).

Figure 2:
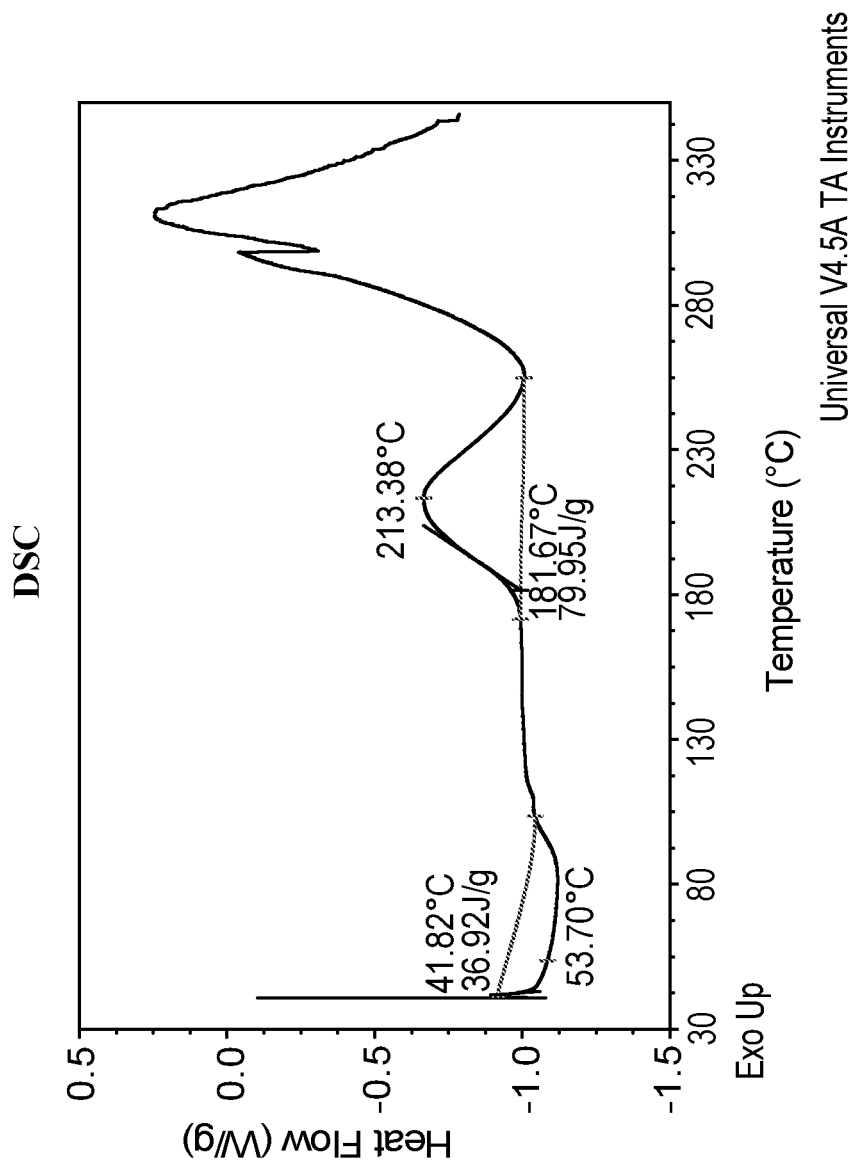
FIG. 2 shows a DSC thermogram for Compound 1-(S) amorphous powder.

In some embodiments, the solid form of the invention is characterized by a DSC (differential scanning calorimetry) thermogram substantially as shown in FIG. 2. As can be seen in FIG. 2, the DSC is characterized by an exothermic peak at about 213° C. which is believed to correspond to a decomposition event. In some embodiments, the DSC is characterized by an exothermic peak with an onset at about 182° C. The DSC is obtained from TA Instruments Differential Scanning calorimetry, Model Q200 with autosampler (see Example 3).

In some embodiments, the solid form of the invention has a glass transition temperature (Tg) of about 106° C. The glass transition temperature is determined by modulated DSC (MDSC) using TA Instruments Differential Scanning calorimetry, Model Q2000 with autosampler.

The solid form of the invention can be prepared in high purity. Purity values presented herein indicate the percentage of the amount of sample that is e.g., Compound 1-(S) (including stereoisomers thereof). Purity values can be determined, for example, by HPLC/UV methods. In some embodiments, the amorphous form of the invention has a purity greater than about 90%, greater than about 95%, greater than about 97%, greater than about 98%, greater than about 98.5%, or greater than about 99%. In some embodiments, the amorphous form of the invention is substantially free of impurities, such as decomposition products and/or residual organic solvent. In some embodiments, the primary impurity in the amorphous form of the invention is water, which can be present, for example, in an amount of less than about 5%, less than about 3%, less than about 2%, less, than about 1.5%, less than about 1%, or less than about 0.5%.

The solid form of the invention can be made by initially dissolving Compound 1-(S) in water with the aid of a base (e.g., a strong base). While not wishing to be bound by theory, it is believed that the base (e.g., strong base) assists dissolution of Compound 1-(S) by deprotonation of the weakly acidic cyclic urea group. In this way, a sufficient amount of Compound 1-(S) can be dissolved in aqueous solution for purification. As used herein, the term "aqueous solution" refers to a solvent system comprised primarily of water. In some embodiments, the aqueous solution is free from organic substances, such as organic solvents, with the exception of Compound 1-(S). In some embodiments, the aqueous solution may contain acids and/or bases, such as inorganic acids and/or bases. Additionally, the aqueous solution may contain one or more salts or ions, such as inorganic salts or ions.

After the Compound 1-(S) is dissolved, the highly basic solution is acidified, which reduces the solubility of Compound 1-(S) and causes it to precipitate out of the aqueous solution into a non-crystalline, homogenous powder which is amenable to use in the formulation of drug products. This process does not require the use of any organic solvents, which is advantageous with respect to scale up and environmental concerns, as well as resulting in a drug product substantially free from potentially harmful organic residue.

In some embodiments, the present invention provides a method for preparing (4S)-7-(3,5-dimethylisoxazol-4-yl)-4-pyridin-2-yl-4,5-dihydroimidazo[1,5,4-de][1,4]benzoxazin-2(1H)-one (Compound 1-(S)) in the form of an amorphous powder comprising precipitating Compound 1-(S) from an aqueous solution comprising Compound 1-(S).

The aqueous solution is initially basic, having a pH greater than 7, such as from about 10-14, about 11-13, or about 12-13. The aqueous solution can be made basic by the addition of base, such as a strong base. Examples of bases include NaOH, KOH, LiOH, and CsOH. In some embodiments, the base is NaOH. Precipitation of Compound 1-(S) is carried out by acidification of the basic aqueous solution in which Compound 1-(S) is dissolved. The acidification can be carried out by addition of acid, such as a strong acid. Examples of acids include HCl, HBr, $H_2SO_4$, $H_3PO_4$, methanesulfonic acid ($CH_3SO_3H$), and toluenesulfonic acid (pTsOH). In some embodiments, the acid is HCl. Acidification may result in an aqueous solution having a final pH below 7, such as a pH about 1-5, about 1-4, or about 2-4.

In some embodiments, the present invention provides a method for preparing (4S)-7-(3,5-dimethylisoxazol-4-yl)-4-pyridin-2-yl-4,5-dihydroimidazo[1,5,4-de][1,4]benzoxazin-2(1H)-one (Compound 1-(S)) in the form of an amorphous powder, comprising:

a) dissolving Compound 1-(S) in a solvent system comprising water and a base (e.g., a strong base) to form a basic aqueous solution;

b) adding an acid (e.g., a strong acid) to the basic aqueous solution (e.g., in an amount effective to lower the pH below about 7) to precipitate the Compound 1-(S) as an amorphous powder.

In one embodiment, the step of adding converts the basic solution to an acidic solution having a pH below about 7.

In some embodiments, the base comprises NaOH.

In some embodiments, the solvent system comprising water and a base (e.g., a strong base) is substantially free of organic solvent.

In some embodiments, the solvent system comprising water and a base (e.g., a strong base) is substantially free of any organic molecules, except for Compound 1-(S) and stereoisomers thereof.

In some embodiments, the basic aqueous solution has a pH of about 10-14.

In some embodiments, the basic aqueous solution has a pH of about 12-13.

In some embodiments, the basic aqueous solution is filtered prior to adding an acid (e.g., a strong acid).

In some embodiments, the acid comprises HCl.

In some embodiments, adding the acid lowers the pH of the aqueous solution to a pH of about 1-5

In some embodiments, adding the acid lowers the pH of the aqueous solution to a pH of about 2-4.

In some embodiments, the present invention provides a solid form of Compound 1-(S) which is prepared by any of the methods described herein.

The present invention also provides a compound, wherein the compound is 5-nitro-3-(pyridin-2-yl)-3,4-dihydro-2H-benzo[b][1,4]oxazin-3-ol (Compound 1x) or a salt thereof (e.g., a pharmaceutically acceptable salt thereof). Compound 1x or a salt thereof can be prepared in high purity. Purity values can be determined, for example, by HPLC/UV methods. In some embodiments, Compound 1x or a salt thereof has a purity greater than about 90%, greater than about 95%, greater than about 97%, greater than about 98%, or greater than about 99%.

The present invention also provides a compound, wherein the compound is 7-iodo-4-pyridin-2-yl-4,5-dihydroimidazo [1,5,4-de][1,4]benzoxazin-2(1H)-one (Compound 4x) or a salt thereof (e.g., a pharmaceutically acceptable salt thereof). Compound 4x or a salt thereof can be prepared in high purity. Purity values can be determined, for example, by HPLC/UV methods. In some embodiments, Compound 4x or a salt thereof has a purity greater than about 90%, greater than about 95%, greater than about 97%, greater than about 98%, or greater than about 99%.

In some embodiment, the present invention also provides a method for preparing Compound 1-(S), comprising:

reacting 7-iodo-4-pyridin-2-yl-4,5-dihydroimidazo[1,5,4-de][1,4]benzoxazin-2(1H)-one (Compound 4x) with (3,5-dimethylisoxazol-4-yl)boronic acid to afford 7-(3,5-dimethylisoxazol-4-yl)-4-pyridin-2-yl-4,5-dihydroimidazo[1,5,4-de][1,4]benzoxazin-2(1H)-one (Compound 1) in the presence of a palladium complex; and separating the S enantiomer of Compound 1 using chiral column chromatography to afford Compound 1-(S).

The present invention also provides a method for preparing Compound 1-(S), comprising the steps of:

1) reacting 2-bromo-1-pyridin-2-ylethanone hydrobromide with 2-amino-nitrophenol in the presence of a base and an organic solvent to afford 5-nitro-3-(pyridin-2-yl)-3,4-dihydro-2H-benzo[b][1,4]oxazin-3-ol (Compound 1x);

2) reacting Compound 1x with hydrogen in the presence of palladium on carbon and an organic solvent to afford 3-(pyridin-2-yl)-3,4-dihydro-2H-benzo[b][1,4]oxazin-5-amine (Compound 2x);

3) reacting Compound 2x with N,N-carbonyldiimidazole in the presence of an organic solvent to afford 4-pyridin-2-yl-4,5-dihydroimidazo[1,5,4-de][1,4]benzoxazin-2(1H)-one (Compound 3x);

4) reacting Compound 3x with N-iodosuccinimide to afford 7-iodo-4-pyridin-2-yl-4,5-dihydroimidazo[1,5,4-de][1,4]benzoxazin-2(1H)-one (Compound 4x);

5) reacting Compound 4x with (3,5-dimethylisoxazol-4-yl)boronic acid in the presence of a palladium complex to afford 7-(3,5-dimethylisoxazol-4-yl)-4-pyridin-2-yl-4,5-dihydroimidazo[1,5,4-de][1,4]benzoxazin-2(1H)-one (Compound 1); and 6) separating the S enantiomer of Compound 1 through chiral column chromatography to afford Compound 1-(S).

In step 1, 2-bromo-1-pyridin-2-ylethanone hydrobromide is reacted with 2-amino-nitrophenol in the presence of a base and an organic solvent to afford 5-nitro-3-(pyridin-2-yl)-3,4-dihydro-2H-benzo[b][1,4]oxazin-3-ol (Compound 1x). In some embodiments, the present invention also provides a method for preparing 5-nitro-3-(pyridin-2-yl)-3,4-dihydro-2H-benzo[b][1,4]oxazin-3-ol (Compound 1x), comprising reacting 2-bromo-1-pyridin-2-ylethanone hydrobromide with 2-amino-nitrophenol in the presence of a base and an organic solvent. In some embodiments, the base is $K_2CO_3$. In some embodiments, the organic solvent is acetonitrile.

In step 2, Compound 1x is reacted with hydrogen in the presence of palladium on carbon and an organic solvent to afford Compound 2x. In some embodiments, the solvent is methanol.

In step 3, Compound 2x is reacted with N,N-carbonyldiimidazole in the presence of an organic solvent to afford Compound 3x. In some embodiments, the organic solvent is ethyl acetate.

In step 4, Compound 3x is reacted with N-iodosuccinimide (NIS) to afford Compound 4x. In some embodiments, the present invention provides a method for preparing 7-iodo-4-pyridin-2-yl-4,5-dihydroimidazo[1,5,4-de][1,4]benzoxazin-2(1H)-one (Compound 4x), comprising reacting 4-pyridin-2-yl-4,5-dihydroimidazo[1,5,4-de][1,4]benzoxazin-2(1H)-one (Compound 3x) with N-iodosuccinimide (NIS). In some embodiments, the reacting is carried out in the presence of an organic solvent and an acid. In some embodiments, the organic solvent is N,N-dimethyl-acetamide. In some embodiments, the acid is sulfuric acid. In some embodiments, the amount of sulfuric acid is about 0.1-0.5 molar equivalent of Compound 3x. In some embodiments, the amount of sulfuric acid is about 0.1, about 0.2, about 0.3, about 0.4, or about 0.5 molar equivalent of Compound 3x. In some embodiments, the amount of sulfuric acid is about 0.3 molar equivalent of Compound 3x.

Using NIS in step 4 provides certain advantages over other halogenation reagents, for example, N-bromosuccinimide (NBS). While not wishing to be bound by theory, NIS is believed to improve the regioselectivity of the resulting product. For example, if NBS is used in this electrophilic bromination reaction, the ratio of the desired (para-) regioisomer to the undesired (ortho-) regioisomer is about 5 to 1. By comparison, using NIS in step 4 has an improved ratio of about 10 to 1. It is believed that because NBS is more reactive than NIS, NBS generally provides a lower regioselectivity towards electrophilic halogenation reaction on the activated aromatic substrate. Another advantage of using NIS is that the resulting aryliodide compound provides a faster and clean Suzuki coupling reaction in the subsequent step as compared to e.g., the corresponding arylbromo compound.

In step 5, Compound 4x is reacted with (3,5-dimethylisoxazol-4-yl)boronic acid in the presence of a palladium complex to afford Compound 1. In some embodiments, the present invention provides a method for preparing 7-(3,5-dimethylisoxazol-4-yl)-4-pyridin-2-yl-4,5-dihydroimidazo [1,5,4-de][1,4]benzoxazin-2(1H)-one (Compound 1), comprising reacting 7-iodo-4-pyridin-2-yl-4,5-dihydroimidazo [1,5,4-de][1,4]benzoxazin-2(1H)-one (Compound 4x) with (3,5-dimethylisoxazol-4-yl)boronic acid in the presence of a palladium complex. In some embodiments, the reacting is carried out in the presence of an aqueous CsF solution and an organic solvent. In some embodiments, the amount of palladium complex is about 0.001-0.010 molar equivalent of Compound 4x. In some embodiments, the amount of palladium complex is about 0.001, about 0.002, about 0.003, about 0.004, about 0.005, about 0.006, about 0.007, about 0.008, about 0.009, or about 0.010 molar equivalent of Compound 4x. In some embodiments, the palladium complex is dichlorobis(p-dimethylamino phenylditbutylphosphine)palladium(II). In some embodiments, the organic solvent is n-butanol.

Using (3,5-dimethylisoxazol-4-yl)boronic acid instead of the corresponding pinacol ester has certain advantages, especially on large scale processes. For example, boronic acid is usually more reactive than its pinacol ester and thus, less reaction time; (3,5-dimethylisoxazole)boronic acid is commercially available and economically less expensive; the boronic acid is a white solid which is easier to handle (e.g., shipping and charging, etc.).

In step 6, Compound 1 is purified through chiral column chromatography to afford Compound 1-(S). Compound 1 in acetonitrile is loaded onto the column, which is eluted with acetonitrile. The chiral purity of the fractions containing Compound 1-(S) is determined by chiral HPLC. After removal of acetonitrile from the fraction containing Compound 1-(S) to afford a crude Compound 1-(S), the sample is further purified by dissolving in methanol and loaded onto the same chiral column, which is eluted with methanol. The desired fraction containing Compound 1-(S) is collected and the solvent is removed under reduced pressure to afford Compound 1-(S).

As used herein, the term "organic solvent" refers to carbon-based solvents (i.e., they contain carbon in their structure) that are employed to dissolve or disperse one or more compounds described herein. Examples of organic solvents include but not limited to acetone, acetic acid, acetonitrile, benzene, carbon tetrachloride, chloroform, dimethyl sulfoxide, methanol, methyl t-butyl ether, methylene chloride, N,N-dimethylformamide, pentane, ethanol, ethyl acetate, hexanes, isopropanol, tetrahydrofuran, and toluene.

As used herein, the term "solvent system" refers to a system which comprises one or more solvents. The system may also contain one or more reagents or starting materials used to prepare a particular compound. In some embodiments, the system may contain primary of water or organic solvents. The system may also contain acids and/or bases, such as inorganic acids and/or bases.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include all isotopes of atoms occurring in the intermediates or final compounds. Isotopes include those atoms having the same atomic number but different mass numbers. Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

Temperature values in connection with DSC, TGA, or other thermal experiments can vary about ±3° C. depending on the instrument, particular settings, sample preparation, etc. Accordingly, a solid form reported herein having a DSC thermogram "substantially" as shown in any of the Figures is understood to accommodate such variation. Additionally, the recitation of temperature values together with the term "about" for peaks or other events in connection with a thermogram also accommodates such variation.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes salts (e.g., pharmaceutically acceptable salts) of the compounds described herein. As used herein, "salts" refers to derivatives of the disclosed compounds wherein the parent compound is modified by converting an existing acid or base moiety to its salt form. Examples of salts include, but are not limited to, mineral or organic acid salts of basic residues such as amines; alkali or organic salts of acidic residues such as carboxylic acids; and the like. The salts of the present invention include the conventional non-toxic salts of the parent compound formed, for example, from non-toxic inorganic or organic acids. The salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences, 17th* Ed., (Mack Publishing Company, Easton, 1985), p. 1418, Berge et al., *J. Pharm. Sci.,* 1977, 66(1), 1-19, and in Stahl et al., *Handbook of Pharmaceutical Salts: Properties, Selection, and Use,* (Wiley, 2002). In some embodiments, the compounds described herein include the N-oxide forms.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography—mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); µg (microgram(s)); µL (microliter(s)); µM (micromolar); wt % (weight percent).

Methods of Use

Compound 1-(S) is a BET protein inhibitor and, thus, is useful in treating and/or preventing diseases and disorders associated with activity of BET proteins. For example, Compound 1-(S) can inhibit one or more of BET proteins BRD2, BRD3, BRD4, and BRD-t. In some embodiments, Compound 1-(S) selectively inhibits one or more BET proteins over another. "Selective" means that the compound binds to or inhibits a BET protein with greater affinity or potency, respectively, compared to a reference, such as another BET protein.

The solid form of Compound 1-(S) described herein is therefore useful for treating and/or preventing BET-mediated disorders. The term "BET-mediated disorder" refers to any disease or condition in which one or more of the BET proteins, such as BRD2, BRD3, BRD4 and/or BRD-t, or a mutant thereof, plays a role, or where the disease or condition is associated with expression or activity of one or more of the BET proteins. The solid form of Compound 1-(S) described herein can be used to treat or lessen the severity of diseases and conditions where BET proteins, such as BRD2, BRD3, BRD4, and/or BRD-t, or a mutant thereof, are known to play a role.

Diseases and conditions treatable and/or preventable using the solid form provided herein include cancer and other proliferative disorders, autoimmune disease, chronic inflammatory diseases, acute inflammatory diseases, sepsis, and viral infection. The diseases can be treated by administering to an individual (e.g., a patient) in need of the treatment a therapeutically effective amount or dose of a solid form of Compound 1-(S) described herein, or any of the embodiments thereof, or a pharmaceutical composition thereof.

In some embodiments, the present invention provides a method of inhibiting a BET protein comprising contacting the BET protein with the solid form provided herein.

In some embodiments, the present invention provides a method of treating cancer in a patient, comprising administering to the patient a therapeutically effective amount of the solid form provided herein. The cancers can include adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

In some embodiments, the present invention provides a method of treating a solid tumor in a patient, comprising administering to the patient a therapeutically effective amount of the solid form provided herein.

In some embodiments, the present invention provides a method of treating colorectal cancer, lung cancer, pancreatic cancer, prostate cancer, or breast cancer in a patient, comprising administering to the patient a therapeutically effective amount of the solid form provided herein.

In some embodiments, the present invention provides a method of treating lymphoma in a patient, comprising administering to the patient a therapeutically effective amount of the solid form provided herein. In some embodiments, the lymphoma is diffuse large B-cell lymphoma (DLBCL).

In some embodiments, the present invention provides a method of treating leukemia in a patient, comprising administering to the patient a therapeutically effective amount of the solid form provided herein. In some embodiments, the leukemia is acute myeloid leukemia (AML), chronic myeloid leukemia (CML), atypical chronic myeloid leukemia (aCML), or chronic myelomonocytic leukemia (CMML).

In some embodiments, the present invention provides a method of treating myelodysplastic syndrome (MDS), myelodysplastic/myeloproliferative neoplasms (MDS/MPN), myelofibrosis (MF), multiple myeloma (MM), or refractory anemia with ringed sideroblasts associated with marked thrombocytosis (RARS-T) in a patient, comprising administering to the patient a therapeutically effective amount of the solid form provided herein.

In some embodiments, the present invention provides a method of treating NUT midline carcinoma in a patient, comprising administering to the patient a therapeutically effective amount of the solid form provided herein.

The diseases treatable using the solid form provided herein also include MYC dependent cancers wherein the cancer is associated with at least one of myc RNA expression or MYC protein expression. A patient can be identified for such treatment by determining myc RNA expression or MYC protein expression in the cancerous tissue or cells.

Diseases that can be treated with the solid form provided herein also include non-cancerous proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The diseases and conditions that can be treated with the solid form provided herein also include chronic autoimmune and inflammatory conditions. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthriti, satopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis nodosa, psoriasis, retinitis, scleritis, scleracierma, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

The diseases and conditions that can be treated with the solid form provided herein also include diseases and conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

The diseases for which the solid form provided herein are indicated also include diseases associated with a systemic inflammatory response syndrome, such as sepsis, burns, pancreatitis, major trauma, hemorrhage and ischemia. The solid form provided herein can be administered to reduce the incidence of: SIRS, the onset of shock, multi-organ dysfunction syndrome, which includes the onset of acute lung injury, ARDS, acute renal, hepatic, cardiac and gastrointestinal injury and mortality. For example, the compounds of the invention can be administered prior to surgical or other procedures associated with a high risk of sepsis, hemorrhage, extensive tissue damage, SIRS or MODS.

Other diseases that can be treated with the solid form provided herein include viral infections. Examples of viral infections that can be treated include Epstein-Barr virus, hepatitis B virus, hepatitis C virus, herpes virus, human immunodeficiency virus, human papilloma virus, adenovirus, poxvirus and other episome-based DNA viruses. The compounds can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment the solid form provided herein is indicated for the treatment of human papilloma virus infections of skin or cervical epithelia.

The diseases and conditions that can be treated with the solid form provided herein also include conditions that are associated with ischemia-reperfusion injury. Examples of such conditions include, but are not limited to conditions such as myocardial infarction, cerebrovascular ischemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

The solid form provided herein is also useful in the treatment of disorders of lipid metabolism via the regulation of APO-A1 such as hypercholesterolemia, atherosclerosis and Alzheimer's disease.

The solid form provided herein can also be used for the treatment of fibrotic conditions such as idiopathic pulmonary fibrosis, renal fibrosis, post-operative stricture, keloid formation, scleroderma and cardiac fibrosis.

The solid form of provided herein can also be used to treat ophthalmological indications such as dry eye.

As used herein, the term "contacting" refers to the bringing together of indicated moieties in an in vitro system or an in vivo system. For example, "contacting" a BET protein with a compound described herein (e.g., the solid form provided herein) includes the administration of the compound to an individual or patient, such as a human, having a BET protein, as well as, for example, introducing a compound of the invention into a sample containing a cellular or purified preparation containing the BET protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "preventing" or "prevention" refers to preventing a disease, condition or disorder in an individual who may be predisposed to the disease, condition or disorder but does not yet experience or display the pathology or symptomatology of the disease.

Combination Therapies

The solid form provided herein can be used in combination treatments where the solid form of Compound 1-(S) described herein is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Ab1, F1t-3, RAF, FAK, and JAK kinase inhibitors for treatment of BET protein-associated diseases, disorders or conditions. The one or more additional pharmaceutical agents can be administered to a patient simultaneously or sequentially.

In some embodiments, the solid form provided herein can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating autoimmune or inflammatory conditions, the solid form provided herein can be administered in combination with a corticosteroid such as triamcinolone, dexamethasone, fluocinolone, cortisone, prednisolone, or flumetholone.

For treating autoimmune or inflammatory conditions, the solid form provided herein can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the solid form provided herein can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the solid form provided herein can be administered in combination with one or more agents selected from an antibiotic, antiviral, antifungal, anesthetic, anti-inflammatory agents including steroidal and non-steroidal anti-inflammatories, and antiallergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which the solid form provided herein may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

In some embodiments, the solid form provided herein can be used in combination with one or more therapeutic agents selected from: Janus kinase inhibitors (e.g., ruxolitinib, tofacitinib, baricitinib, CYT387, GLPG0634, lestaurtinib, pacritinib, TG101348), Pim kinase inhibitors, PI3 kinase inhibitors (including PI3K-delta selective and broad spectrum PI3K inhibitors), MEK inhibitors, cyclin dependent kinase inhibitors, b-RAF inhibitors, mTOR inhibitors, proteasome inhibitors (e.g., bortezomib, carfilzomib), HDAC-inhibitors (e.g., panobinostat, vorinostat), DNA methyl transferase inhibitors, dexamethasone, melphalan, and immunomodulators such as lenolidomide and pomalidomide. In some embodiments, the Janus kinase inhibitor is selective for JAK1. In some embodiments, the Janus kinase inhibitor is selective for JAK1 and JAK2.

In some embodiments, the solid form provided herein can be used in combination with one or more immune checkpoint inhibitors. Exemplary immune checkpoint inhibitors include inhibitors against immune checkpoint molecules such as CD27, CD28, CD40, CD122, OX40, GITR, CD137, ICOS, A2AR, B7-H3, B7-H4, BTLA, CTLA-4, indoleamine 2,3-dioxygenase (IDO), LAG3 TIM3, VISTA, PD-1, PD-L1 and PD-L2 In some embodiments, the solid form provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, or AMP-224. In some embodiments, the anti-PD-1 monoclonal antibody is nivolumab or pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016.

Formulation, Dosage Forms, and Administration

When employed as pharmaceuticals, the solid form provided herein can be administered in the form of pharmaceutical compositions. In some embodiments, the present invention provides a pharmaceutical composition comprising the solid form provided herein and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intra-arterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the solid form provided herein, in combination with one or more pharmaceutically acceptable carriers (excipients). In some embodiments, the present invention provides a solid oral dosage form comprising the solid form provided herein. In some embodiments, the dosage form is in the form of a pill, tablet, or capsule. In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated as a solution or a suspension. Suitable excipients include methyl cellulose (MC), citrate, and D-α-Tocopherol polyethylene glycol 1000 succinate or Vitamin E polyethylene glycol succinate (TPGS). In some embodiments, the concentration of Compound 1-(S) is from about 0.1-5.0 mg/mL, about 0.5-3.0 mg/mL, or about 0.5-2.5 mg/mL. The concentration of Compound 1-(S) is about 0.5 mg/mL or about 2.5 mg/mL.

In some embodiments, the composition is a solution, comprising about 0.5 mg/mL of Compound 1-(S) with about 0.5% MC in water. In some embodiments, the composition is a suspension, comprising about 2.5 mg/mL of Compound 1-(S) with about 0.5% MC in water. In some embodiments, the composition is a solution, comprising about 0.5 mg/mL of Compound 1-(S) with about 0.5% MC in about 50 mM citrate. In some embodiments, the composition is a suspension, comprising about 2.5 mg/mL of Compound 1-(S) with about 0.5% MC in about 50 mM citrate. In some embodiments, the composition is a solution, comprising about 2.5 mg/mL of Compound 1-(S) with about 0% TPGS in about 50 mM citrate.

In preparing a formulation, Compound 1-(S) can be milled to provide the appropriate particle size prior to combining with the other ingredients. Compound 1-(S) may be milled using known milling procedures such as wet milling to obtain a particle size appropriate for tablet formation and for other formulation types. Finely divided (nanoparticulate) preparations of Compound 1-(S) can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the solid form provided herein. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the solid form provided herein. One having ordinary skill in the art will appreciate that this embodies Compound 1-(S) and compositions thereof containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of Compound 1-(S).

In some embodiments, the compositions of the invention contain from about 50 mg to about 500 mg of the solid form provided herein. One having ordinary skill in the art will appreciate that this embodies Compound 1-(S) and compositions thereof containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of Compound 1-(S).

In some embodiments, the compositions of the invention contain from about 500 mg to about 1,000 mg of the solid form provided herein. One having ordinary skill in the art will appreciate that this embodies Compound 1-(S) and compositions thereof containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of Compound 1-(S).

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, Compound 1-(S) is mixed with a pharmaceutical excipient to form a solid preformulation composition containing a homogeneous mixture of Compound 1-(S). When referring to these preformulation compositions as homogeneous, Compound 1-(S) is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of Compound 1-(S).

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which Compound 1-(S) and compositions thereof can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of Compound 1-(S). The topical formulations can be suitably packaged in tubes of, for example, 100 g which are optionally associated with instructions for the treatment of the select indication, e.g., psoriasis or other skin condition.

The amount of Compound 1-(S) and compositions thereof administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. It will be understood that use of certain of the foregoing excipients, carriers, or stabilizers will result in the formation of pharmaceutical salts.

The therapeutic dosage of Compound 1-(S) can vary according to, for example, the particular use for which the treatment is made, the manner of administration of the compound, the health and condition of the patient, and the judgment of the prescribing physician. The proportion or concentration of Compound 1-(S) in a pharmaceutical composition can vary depending upon a number of factors including dosage, chemical characteristics (e.g., hydrophobicity), and the route of administration. For example, Compound 1-(S) can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Kits

The present invention also includes pharmaceutical kits useful, for example, in the treatment or prevention of BET protein-associated diseases or disorders, such as cancer, which include one or more containers containing a pharmaceutical composition comprising a therapeutically effective amount of the solid form provided herein, or any of the embodiments thereof. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Example 1

Preparation of Amorphous Solid Form of Compound 1-(S)

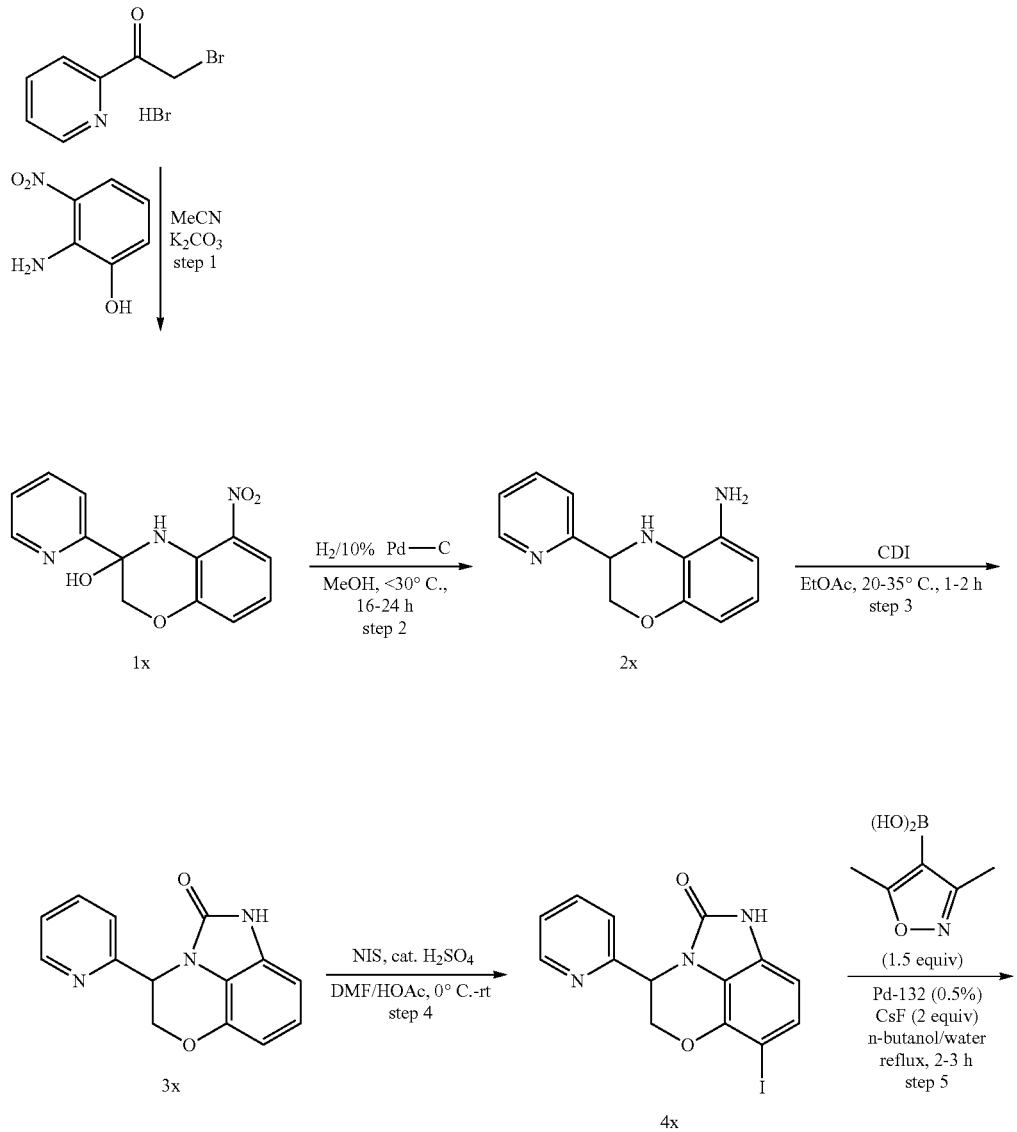

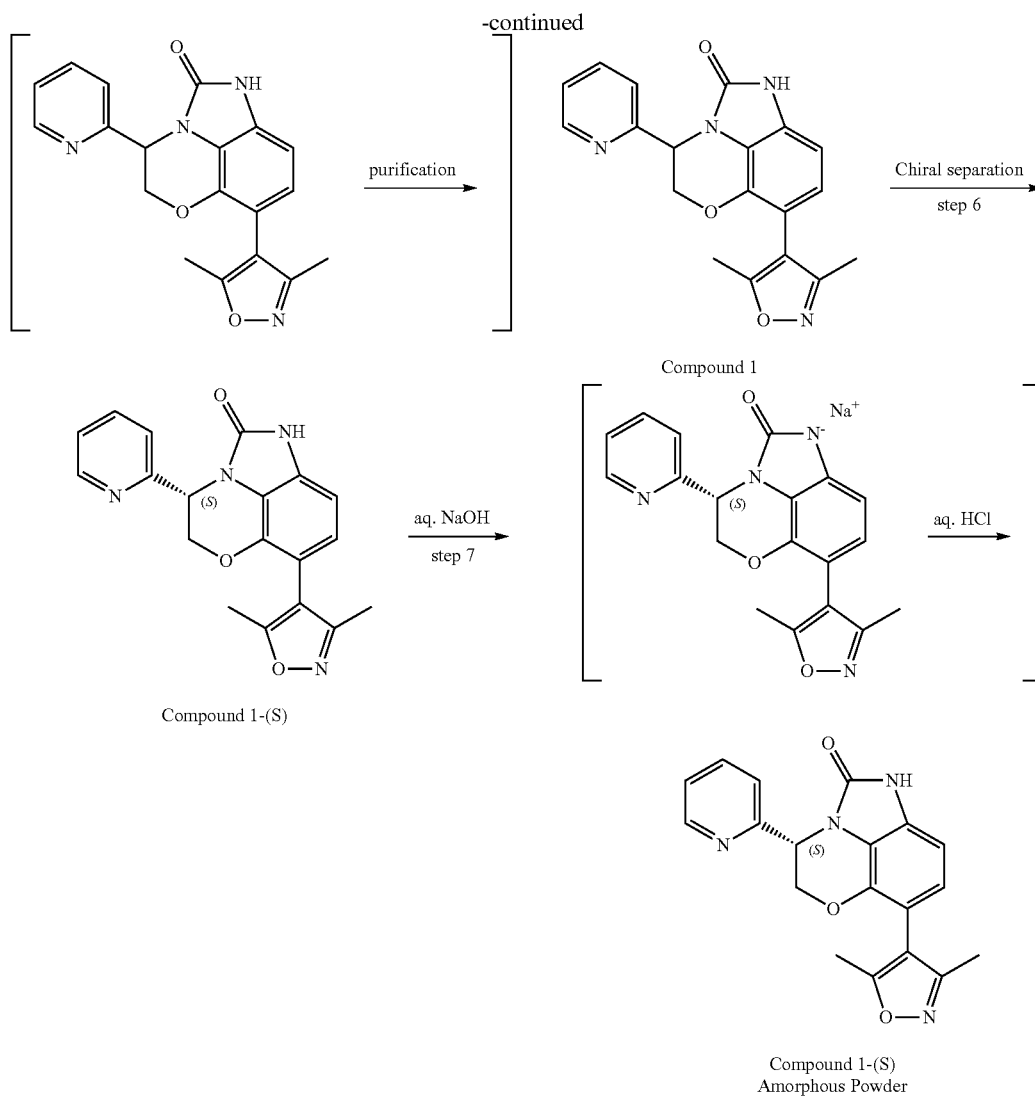

Compound 1

Compound 1-(S)

Compound 1-(S)
Amorphous Powder

Preparation of Starting Material 2-bromo-1-pyridin-2-ylethanone Hydrobromide

Bromine (Br$_2$, 198 g, 1240 mmol) dissolved in acetic acid (100 mL) was added slowly to a mixture of 1-(pyridin-2-yl)ethanone (150 g, 1238 mmol) in acetic acid (1500 mL) at rt. The red reaction solution was heated to 105° C. for 1 hour to give an off-white slurry. The mixture was stirred for 1 hour at rt, cooled in a water bath (caution acetic acid freezes), filtered, then the solids were washed with acetic acid (150 mL) and ethyl acetate (250 mL). The solid was suspended in acetic acid (1500 mL) and heated to 105° C. for 1 h (note: material did not completely dissolve). The reaction was allowed to cool to rt in a water bath. The precipitate was filtered, washed with acetic acid 100 mL and ethyl acetate 300 mL, and dried under house vacuum at rt to give crude 2-bromo-1-pyridin-2-ylethanone hydrobromide (305 g, 87%) as an off-white powder, which was used in the subsequent step without further purification.

Step 1. 5-nitro-3-(pyridin-2-yl)-3,4-dihydro-2H-benzo[b][1,4]oxazin-3-ol (1×)

2-Bromo-1-pyridin-2-ylethanone hydrobromide (135 g, 480 mmol) was suspended in acetonitrile (1700 mL) at rt and potassium carbonate (135 g, 977 mmol) was added. The reaction was stirred for 1 h and then was heated to 60° C. and 2-amino-3-nitrophenol (67.5 g, 438 mmol) was added slowly portionwise as a solid over 30 minutes. The reaction became a dark red slurry. This mixture was stirred at 60° C. for an additional 1 h. The reaction was diluted with water (6500 mL) and stirred vigorously for 1 h to give a precipitate. The solids were collected and washed with water and dried to give the product as a dark brown solid 134 g. The solid was suspended in ethyl acetate (2500 mL) and heated to 75° C. in an oil bath to dissolve the product. To the reaction mixture was added activated charcoal (40 g). The mixture was stirred for 30 minutes and filtered hot through celite to give a yellow-red solution. The solution was concentrated in vacuo to give a crystalline residue. This was triturated with ethyl ether, filtered and the solids were washed with ethyl ether to give the crude desire product, 5-nitro-3-(pyridin-2-yl)-3,4-dihydro-2H-benzo[b][1,4]oxazin-3-ol (1×, 100 g, 83%) as a yellow orange crystalline solid. The mother liquor was concentrated to give an additional 10.0 g of the crude desired product as a yellow orange solid. The crude desired product was directly utilized in the subsequent reactions without further purification.

Step 2. 3-(Pyridin-2-yl)-3,4-dihydro-2H-benzo[b][1,4]oxazin-5-amine (2×)

A Parr reactor (18 L) was charged with 5-nitro-3-(pyridin-2-yl)-3,4-dihydro-2H-benzo[b][1,4]oxazin-3-ol (1×, 1000 g, 3.918 mol), methanol (7 L) and 10% palladium on carbon (97 g, 50% wet) at ambient temperature. After a standard nitrogen purge, the vessel was charged with hydrogen (65 psi) and stirred for 16 hours maintaining the internal temperature between 20-25° C. The vessel was recharged with hydrogen 8 times. Once the reaction was complete, the vessel was purged again with nitrogen and the resultant dark solution was filtered through a pad of celite (300 g). The celite filter cake was washed with methanol (6 L) and the combined filtrates were concentrated under reduced pressure. Toluene (8 L) was added and evaporated under reduced pressure to remove water. The residue was purified over silica gel ($SiO_2$, 2 Kg), eluting with a gradient of 50 to 100% ethyl acetate in n-heptane. The solids were triturated with methyl tert-butyl ether (MTBE, 1 L) and filtered to give the first crop of the desired product (2×, 447 g) as off-white to yellow solids. The filtrates were re-chromatographed and triturated with MTBE to give the second crop of the desired product (2×, 145 g) as off-white to yellow solids. The total amount of desired product (2×) isolated was 592 g (66.5% yield, 99% purity). $^1$H-NMR (300 MHz, DMSO-$d_6$) δ 8.60-8.56 (m, 1H), 7.83-7.76 (m, 1H), 7.5-7.47 (m, 1H), 7.34-7.29 (m, 1H), 6.42-6.36 (m, 1H), 6.28-6.24 (m, 1H), 6.10-6.06 (m, 1H), 5.15-5.13 (m, 1H) 4.69 (s, 2H), 4.58-4.54 (m, 1H), 4.29-4.24 (m, 1H), 4.14-4.08 (m, 1H); $C_{13}H_{13}N_3O$ (MW: 227.26), LCMS (EI) m/e 228 ($M^+$+H).

Step 3. 4-Pyridin-2-yl-4,5-dihydroimidazo[1,5,4-de][1,4]benzoxazin-2(1H)-one (3×)

A suspension of 3-(pyridin-2-yl)-3,4-dihydro-2H-benzo[b][1,4]oxazin-5-amine (2×, 10 g, 0.044 mole, 1.0 equiv) in ethyl acetate (120 mL) was heated to 40-50° C. and stirred at 40-50° C. until a solution was obtained. The resulting solution was gradually cooled down to 15-30° C. before N,N-carbonyldiimidazole (CDI, 8.55 g, 0.0528 mole, 1.2 equiv) was added. The resulting reaction mixture was stirred at 15-40° C. for at least 30 minutes and the desired product (3×) precipitated out during the reaction. When HPLC showed the reaction was complete ((2×)≤0.5%), the solids were collected by filtration and washed sequentially with MTBE (20 mL), water (2×25 mL), and MTBE (20 mL). The wet cake was dried on the filter for at least 3 hours, and then dried at 20-60° C. under vacuum to afford 4-pyridin-2-yl-4,5-dihydroimidazo[1,5,4-de][1,4]benzoxazin-2(1H)-one (3×, 9.92 g, 89% yield) as off-white solids. $^1$H-NMR (400 MHz, DMSO-$d_6$) δ 10.91 (s, 1H), 8.51 (d, J=4.1 Hz, 1H), 7.74 (td, J=7.7, 1.8 Hz, 1H), 7.29 (dd, J=6.8, 4.9 Hz, 1H), 7.01 (d, J=7.9 Hz, 1H), 6.85 (t, J=8.0 Hz, 1H), 6.67 (d, J=7.7 Hz, 1H), 6.52 (d, J=8.1 Hz, 1H), 5.48 (s, 1H), 4.75 (dd, J=11.5, 1.9 Hz, 1H), 4.39 (dd, J=11.5, 3.1 Hz, 1H) ppm; $^{13}$C NMR (101 MHz, DMSO-$d_6$) δ 157.24, 153.53, 150.04, 141.07, 137.90, 128.65, 123.64, 121.75, 121.41, 118.18, 107.10, 103.33, 70.89, 54.55 ppm; $C_{14}H_{11}N_3O_2$ (MW: 253.26), LCMS (EI) m/e 254 ($M^+$+H).

Step 4. 7-Iodo-4-pyridin-2-yl-4,5-dihydroimidazo[1,5,4-de][1,4]benzoxazin-2(1H)-one (4×)

A solution of 4-pyridin-2-yl-4,5-dihydroimidazo[1,5,4-de][1,4]benzoxazin-2(1H)-one (3×, 25 g, 0.0987 mole) in N,N-dimethyl-acetamide (DMF, 300 ml) was stirred at 15-30° C. for 15 minutes. N-Iodosuccinimide (NIS, 24.43 g, 0.1086 mole, 1.10 equiv) was charged to the reaction mixture and the resulting reaction mixture was stirred at 15-30° C. for 12-60 hours until the starting material 4-pyridin-2-yl-4,5-dihydroimidazo[1,5,4-de][1,4]benzoxazin-2(1H)-one (3×) was less than 10% by HPLC. Sulfuric acid ($H_2SO_4$, 1.58 mL, 0.003 mole, 0.30 equiv) was then added while maintaining the batch at 15-30° C. The reaction mixture was stirred at 15-30° C. until starting material (3×) was less than 2%. The reaction mixture was then cooled to 5-15° C. before an 1 N aqueous sodium hydroxide (55.3 ml, 0.0553 mole, 0.56 equiv) solution was added to adjust the reaction mixture pH to 4 to 7 while maintaining the reaction temperature below 35° C. The resulting mixture was continuing to stir at 15-35° C. for at least 30 minutes and water (50 mL) was added at 15-35° C. The resulting mixture was stirred at ambient temperature until a precipitate was observed. An additional amount of water (250 mL) was added to the mixture and the resulting suspension was stirred at ambient temperature for at least 1 hour before the solid was filtered. The filter cake was washed sequentially with water (300 mL) and MTBE (175 mL). The wet cake was dried on the filter to afford 7-iodo-4-pyridin-2-yl-4,5-dihydroimidazo[1,5,4-de][1,4]benzoxazin-2(1H)-one (4×, 31.4 g, 84% yield) as yellow to brown solids. $^1$H NMR (400 MHz, DMSO-$d_6$) δ 11.03 (s, 1H), 8.50 (m, 1H), 7.76 (td, J=7.7, 1.8 Hz, 1H), 7.31 (dd, J=6.8, 4.9 Hz, 1H), 7.22 (d, J=7.9 Hz, 1H), 7.10 (d, J=7.9 Hz, 1H), 6.57 (t, J=8.2 Hz, 1H), 5.51 (s, 1H), 4.86 (dd, J=11.5, 1.8 Hz, 1H), 4.46 (dd, J=11.5, 3.1 Hz, 1H) ppm; $^{13}$C NMR (101 MHz, DMSO-$d_6$) δ 156.85, 153.09, 150.04, 140.99, 138.00, 129.81, 128.78, 123.77, 121.59, 118.69, 105.93, 71.85, 70.86, 54.37 ppm; $C_{14}H_{10}N_3O_2$ (MW: 379.15), LCMS (EI) m/e 380 ($M^+$+H).

Step 5. 7-(3,5-Dimethylisoxazol-4-yl)-4-pyridin-2-yl-4,5-dihydroimidazo[1,5,4-de][1,4]benzoxazin-2(1H)-one (Compound 1)

1-Butanol (93.5 mL) was degassed by bubbling nitrogen for 5 minutes, then 7-iodo-4-pyridin-2-yl-4,5-dihydroimidazo[1,5,4-de][1,4]benzoxazin-2(1H)-one (4×, 9.74 g, 0.026 mol), (3,5-dimethylisoxazol-4-yl)boronic acid (4.71 g, 0.033 mole, 1.3 equiv), aqueous CsF solution (10.54 g in 16.6 mL of $H_2O$, 0.069 mole, 2.7 equiv) and dichlorobis(p-dimethylamino phenylditbutylphosphine)palladium(II) (Pd-132) (0.091 g, 0.00013 mole, 0.005 equiv) were charged to the reactor with nitrogen bubbling. The resulting reaction mixture was further degassed by bubbling nitrogen for 15 minutes before it was heated to 85-95° C. and stirred at 85-95° C. for 1-2 hour. When HPLC indicated reaction completion, the reaction mixture was cooled to 15-30° C. Then EtOAc (50 mL) and water (35 mL) were added, and the resulting mixture was stirred at ambient temperature for 30 minutes. The phases were separated, and the organic phase was concentrated under vacuum. The residue was transferred to a reactor with EtOAc and treated with an aqueous solution of L-cysteine. The resulting mixture was heated to 60-70° C. for 1 hour before being gradually cooled to 15-30° C. The two phases were separated and the organic phase was filtered through celite. The filter cake was washed with EtOAc. The organic phase was transferred to the reactor mixture with an additional amount of aqueous L-cysteine solution and the resulting mixture was heated to 60-70° C. for 1 hour before being cooled down to 15-30° C. The two phases were separated; the organic phase was filtered through celite and the filter cake was washed with EtOAc. The organic phase was then washed with water and concentrated to afford 7-(3,5-dimethylisoxazol-4-yl)-4-pyridin-2-yl-4,5-dihydroimidazo[1,5,4-de][1,4]benzoxazin-2(1H)-one (Compound 1, 8.95 g, 98.8% yield) as yellow to brown solids. $^1$H NMR (400 MHz, DMSO-d$_6$) δ 11.00 (s, 1H), 8.49 (m, 1H), 7.76 (td, J=7.7, 1.8 Hz, 1H), 7.29 (ddd, J=7.5, 4.8, 0.9 Hz, 1H), 7.11 (d, J=8.0 Hz, 1H), 6.79 (m, 2H), 5.52 (t, J=2.3 Hz, 1H), 4.76 (dd, J=11.4, 2.0 Hz, 1H), 4.43 (dd, J=11.4, 3.1 Hz, 1H), 2.20 (s, 3H), 2.03 (s, 3H) ppm; $^{13}$C NMR (101 MHz, DMSO-d$_6$) δ 166.13, 159.55, 157.12, 153.56, 149.97, 138.81, 137.90, 128.45, 123.70, 123.31, 121.56, 118.66, 112.14, 108.91, 103.56, 71.07, 54.37, 11.98, 10.90 ppm; $C_{19}H_{16}N_4O_3$ (MW: 348.36), LCMS (EI) m/e 349 (M$^+$+H).

Step 6. (4S)-7-(3,5-Dimethylisoxazol-4-yl)-4-pyridin-2-yl-4,5-dihydroimidazo[1,5,4-de][1,4]benzoxazin-2(1H)-one (Compound 1-(S))

In an 8×50 mm Simulated Moving Bed (SMB) separation unit, the columns packed with 20-micron Chiralpak AS chiral stationary phase (CSP) were installed. The columns and the SMB system were then flushed with acetonitrile. A solution of 7-(3,5-dimethylisoxazol-4-yl)-4-pyridin-2-yl-4,5-dihydroimidazo[1,5,4-de][1,4]benzoxazin-2(1H)-one (Compound 1, 5500 g) in acetonitrile was then loaded onto the chiral columns installed in the SMB unit. The chiral columns were then eluted with acetonitrile. The fractions containing the desired Compound 1-(S) and meeting the chiral purity criterion as determined by chiral HPLC were collected and combined for concentration under reduced pressure. After removal of acetonitrile, the crude desired product, (4S)-7-(3,5-dimethylisoxazol-4-yl)-4-pyridin-2-yl-4,5-dihydroimidazo[1,5,4-de][1,4]benzoxazin-2(1H)-one (Compound 1-(S), 2500 g, 45.5%) was obtained for further purification. The fractions containing the undesired (R)-enantiomer as determined by chiral HPLC, were collected and combined for concentration under reduced pressure to afford the crude undesired product, for other use. The crude Compound 1-(S) obtained from the chiral separation was then dissolved in methanol and the resulting methanol solution was loaded onto the same chiral columns installed in the same SMB unit. The chiral columns were eluted with methanol. The fractions containing the desired product and meeting the chemical purity criterion as determined by HPLC and chiral HPLC were collected, combined for concentration under reduced pressure. After removal methanol, the pure desired product, (4S)-7-(3,5-dimethylisoxazol-4-yl)-4-pyridin-2-yl-4,5-dihydroimidazo[1,5,4-de][1,4]benzoxazin-2(1H)-one (Compound 1-(S), 2300 g, 41.8% for two separations), was obtained as light yellow oil, which was solidified under vacuum at ambient temperature. This material was used directly in the subsequent process steps to manufacture amorphous Compound 1-(S) free base drug substance.

Step 7. (4S)-7-(3,5-Dimethylisoxazol-4-yl)-4-pyridin-2-yl-4,5-dihydroimidazo[1,5,4-de][1,4]benzoxazin-2(1H)-one (Amorphous Compound 1-(S))

A suspension of (4S)-7-(3,5-dimethylisoxazol-4-yl)-4-pyridin-2-yl-4,5-dihydroimidazo[1,5,4-de][1,4]benzoxazin-2(1H)-one (Compound 1-(S), 42.86 g, 0.123 mole) in water (429 mL) was cooled to 0-5° C. A 1 M aqueous NaOH solution (123 mL, 0.123 mole, 1.0 equiv) was then added to the suspension while maintaining the internal temperature at 0-5° C. The reaction mixture (at pH 12-13) was then gradually warmed to 10-25° C. and stirred at 10-25° C. until a clear solution was obtained. The solution was polish filtered, and rinsed through the filter with a 0.25 M aqueous NaOH solution (20 mL, 0.005 mole, 0.04 equiv). The filtered solution was then cooled to 0-5° C. before being treated with an 1 M aqueous HCl solution (128 mL, 0.128 mole, 1.04 equiv) at 0-5° C. The final pH of the reaction mixture was 2-4. The solid product was gradually precipitated out during acidification and the resulting suspension was gradually warmed to ambient temperature and stirred at ambient temperature for 1-2 hours. The solid was collected by filtration and washed sequentially with purified water and n-heptane. The wet cake was dried by pulling vacuum on the filter for 3-10 hours and further dried under vacuum at 30-40° C. to afford (4S)-7-(3,5-dimethylisoxazol-4-yl)-4-pyridin-2-yl-4,5-dihydroimidazo[1,5,4-de][1,4]benzoxazin-2(1H)-one (amorphous Compound 1-(S), 38.8 g, 90.6% yield) as white to off-white amorphous powder. $^1$H NMR (400 MHz, DMSO-d$_6$) δ 11.00 (s, 1H), 8.49 (m, 1H), 7.76 (td, J=7.7, 1.8 Hz, 1H), 7.29 (ddd, J=7.5, 4.8, 0.9 Hz, 1H), 7.11 (d, J=8.0 Hz, 1H), 6.79 (m, 2H), 5.52 (t, J=2.3 Hz, 1H), 4.76 (dd, J=11.4, 2.0 Hz, 1H), 4.43 (dd, J=11.4, 3.1 Hz, 1H), 2.20 (s, 3H), 2.03 (s, 3H) ppm; $^{13}$C NMR (101 MHz, DMSO-d$_6$) δ 166.13, 159.55, 157.12, 153.56, 149.97, 138.81, 137.90, 128.45, 123.70, 123.31, 121.56, 118.66, 112.14, 108.91, 103.56, 71.07, 54.37, 11.98, 10.90 ppm; $C_{19}H_{16}N_4O_3$ (MW: 348.36), LCMS (EI) m/e 349 (M$^+$+H).

Example 2

X-Ray Powder Diffraction (XRPD) of Amorphous Compound 1-(S)

Amorphous Compound 1-(S) was characterized by XRPD. The X-Ray Power Diffraction (XRPD) was obtained from Rigaku MiniFlex X-ray Powder Diffractometer (XRPD). The general experimental procedures for XRPD were: (1) X-ray radiation from copper at 1.054056 Å with K$_β$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min. The XRPD pattern displays an amorphous halo as shown in FIG. 1.

Example 3

Differential Scanning Calorimetry (DSC) of Amorphous Compound 1-(S)

Amorphous Compound 1-(S) was characterized by DSC. The DSC was obtained from TA Instruments Differential Scanning calorimetry, Model Q200 with autosampler. The DSC instrument conditions were as follows: 30-350° C. at 10° C./min; Tzero aluminum sample pan and lid; and nitrogen gas flow at 50 mL/min. The DSC thermogram is shown in FIG. 2. The DSC thermogram revealed one exothermic event at an onset temperature of 181.7° C. with a peak temperature of 213.4° C. which corresponds to the decomposition of the compound. The endothermic event below 100° C. is believed to be due to dehydration. No melting point was observed due to the amorphous nature of the compound.

Example 4

Determination of Glass Transition Temperature of Amorphous Compound 1-(S)

Figure 3:
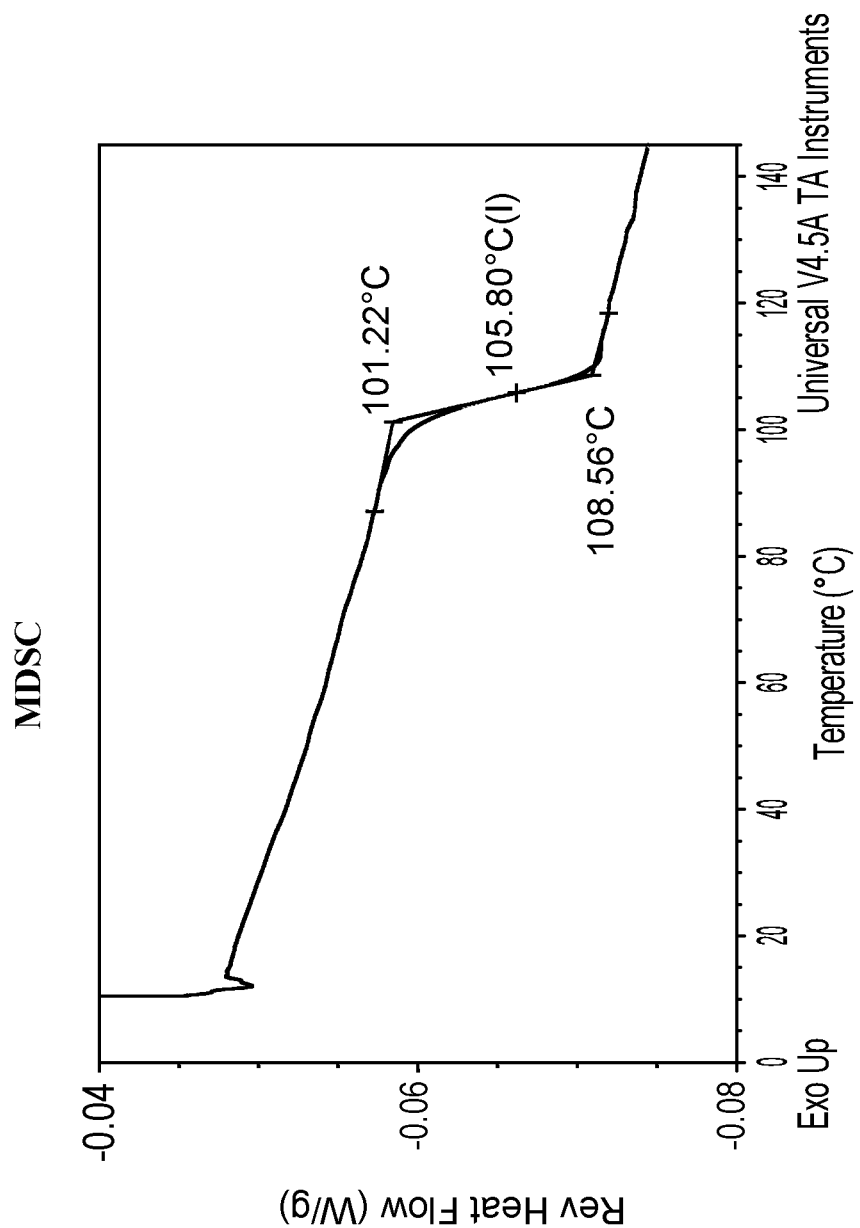
FIG. 3 shows a MIDSC thermogram for Compound 1-(S) amorphous powder.

The glass transition temperature (Tg) was determined to be 105.8° C. by modulated DSC (MDSC) using TA Instruments Differential Scanning calorimetry, Model Q2000 with autosampler. The MDSC instrument conditions were as follows: modulation temperature amplitude: ±1° C.; modulation: 60 second; ramp rate: 2° C./min; temperature range: 10-150° C.; Tzero aluminum sample pan and lid; and nitrogen gas flow at 50 mL/min. The MDSC thermogram is shown in FIG. 3.

Example 5

Stability of Amorphous Compound 1-(S)

Amorphous Compound 1-(S) has been found to be physically stable under elevated temperature and humidity. Table 1 indicates the conditions/time to which the amorphous form was subjected and provides the measured water content (Karl-Fischer analysis) and purity (by HPLC/UV). The HPLC/UV instrument was Agilent HPLC 1100 with an Agilent Zorbax SB-C18, 3.5 μm, 4.6×150 mm column. The HPLC conditions were as follows: column temperature: 40° C.; mobile phase A (MPA): 0.05% (v/v) trifluoroacetic acid (TFA) in water; mobile phase B (MPB): 0.05% (v/v) TFA in acetonitrile; and flow rate: 1 mL/min.

The gradient conditions were as follows:

| Time (minute) | % MPA | % MPB |
| --- | --- | --- |
| 0 | 67 | 23 |
| 20 | 67 | 23 |
| 25 | 20 | 80 |
| 25.1 | 67 | 23 |
| 30 | 67 | 23 |

Injection: 5 μL
Detection: UV 220 nm, 254 nm

TABLE 1

| Conditions | Time (weeks) | Water content (%) | Purity 220 nm (%) | Purity 254 nm (%) | Solid Form (XRPD) |
| --- | --- | --- | --- | --- | --- |
| 50° C. | 0 | 1.67 | 98.22 | 97.10 | Amorphous |
| Open vial | 1 | 0.69 | 98.12 | 97.11 | Not measured |
| | 2 | 0.43 | 98.23 | 97.11 | Amorphous |
| 40° C./75% RH | 0 | 1.67 | 98.22 | 97.10 | Amorphous |
| Open vial | 1 | 3.39 | 98.22 | 97.10 | Not measured |
| | 2 | 2.64 | 98.18 | 97.10 | Amorphous |

Example 6

Formulation of Amorphous Compound 1-(S)

Amorphous Compound 1-(S) was formulated as described in the table below. Table 2 indicates the target concentration, final pH, solubility, and some observation of the resulting formulations.

TABLE 2

| Vehicle | Target Concentration (mg/mL) | Final pH | Solubility (mg/mL) | Observations |
| --- | --- | --- | --- | --- |
| 0.5% MC in water | 0.5 | 6.76 | >0.5 | solution |
| | 2.5 | 7.87 | 0.842 | suspension |
| 0.5% MC in 50 mM citrate, pH 3.0 | 0.5 | 3.00 | >0.5 | solution |
| | 2.5 | 3.03 | 1.15 | suspension |
| 10% TPGS in 50 mM citrate, pH 3.0 | 2.5 | 3.07 | >2.5 | solution |

MC = methyl cellulose; TPGS = D-α-tocopherol polyethylene glycol 1000 succinate or Vitamin E polyethylene glycol succinate.

Various modifications of the invention, in addition to those described herein, will be apparent to those skilled in the art from the foregoing description. Such modifications are also intended to fall within the scope of the appended claims. Each reference cited in the present disclosure, including all patent, patent applications, and publications, is incorporated herein by reference in its entirety.

What is claimed is:

1. A compound wherein the compound is 7-iodo-4-pyridin-2-yl-4,5-dihydroimidazo[1,5,4-de][1,4]benzoxazin-2(1H)-one (Compound 4x).

2. A method for preparing the compound of claim 1, comprising reacting 4-pyridin-2-yl-4,5-dihydroimidazo[1,5,4-de][1,4]benzoxazin-2(1H)-one (Compound 3x) with N-iodosuccinimide.

3. The method of claim 2 wherein the reacting is carried out in the presence of an organic solvent and an acid.

4. The method of claim 3 wherein the organic solvent is N,N-dimethyl-acetamide.

5. The method of claim 3 wherein the acid is sulfuric acid.

6. The method of claim 5 wherein the amount of sulfuric acid is about 0.1-0.5 molar equivalent of Compound 3x.

7. The method of claim 6 wherein the amount of sulfuric acid is about 0.3 molar equivalent of Compound 3x.

8. The method of claim 2 wherein Compound 3x is prepared by reacting 3-(pyridin-2-yl)-3,4-dihydro-2H-benzo[b][1,4]oxazin-5-amine (Compound 2x) with N,N-carbonyldiimidazole in the presence of an organic solvent.

9. The method of claim 8 wherein the organic solvent is ethyl acetate.

10. The method of claim 8 wherein Compound 2x is prepared by reacting 5-nitro-3-(pyridin-2-yl)-3,4-dihydro-2H-benzo[b][1,4]oxazin-3-ol (Compound 1x) with hydrogen in the presence of palladium on carbon and an organic solvent.

11. The method of claim 10 wherein the organic solvent is methanol.

12. The method of claim 10 wherein Compound 1x is prepared by reacting 2-bromo-1-pyridin-2-ylethanone hydrobromide with 2-amino-nitrophenol in the presence of a base and an organic solvent.

13. The method of claim 12 wherein the base is $K_2CO_3$.

14. The method of claim 12 wherein the organic solvent is acetonitrile.

* * * * *

UNITED STATES PATENT AND TRADEMARK OFFICE
CERTIFICATE OF CORRECTION

PATENT NO. : 10,858,372 B2
APPLICATION NO. : 16/425193
DATED : December 8, 2020
INVENTOR(S) : Shili Chen et al.

Page 1 of 1

It is certified that error appears in the above-identified patent and that said Letters Patent is hereby corrected as shown below:

On the Title Page

After Related U.S. Application Data, delete "Continuation of application No. 15/913,248, filed on Mar. 6, 2018, now Pat. No. 10,329,305, which is a division of application No. 15/337,202, filed on Oct. 28, 2016, now abandoned, application No. 16/425,193, which is a division of application No. 15/337,202, filed on Oct. 28, 2016.
Provisional application No. 62/248,040, filed on Oct. 29, 2015." and insert -- "Division of application No. 15/913,248, filed on Mar. 6, 2018, now Pat. No. 10,329,305, which is a division of application No. 15/337,202, filed on Oct. 28, 2016, now abandoned.
Provisional application No. 62/248,040, filed on Oct. 29, 2015." --

Signed and Sealed this
Fourteenth Day of September, 2021

Drew Hirshfeld
*Performing the Functions and Duties of the
Under Secretary of Commerce for Intellectual Property and
Director of the United States Patent and Trademark Office*